US007323301B2

(12) United States Patent
Matsumoto et al.

(10) Patent No.: US 7,323,301 B2
(45) Date of Patent: Jan. 29, 2008

(54) NUCLEIC ACID, PROBE COMPRISING THE NUCLEIC ACID AND SCREENING METHOD USING THE PROBE

(75) Inventors: Naomichi Matsumoto, Nagasaki (JP); Norio Niikawa, Nagasaki (JP)

(73) Assignee: Nagasaki University, Nagasaki (JP)

( * ) Notice: Subject to any disclaimer, the term of this patent is extended or adjusted under 35 U.S.C. 154(b) by 583 days.

(21) Appl. No.: 10/309,933

(22) Filed: Dec. 4, 2002

(65) Prior Publication Data

US 2003/0162203 A1 Aug. 28, 2003

(30) Foreign Application Priority Data

Dec. 19, 2001 (JP) ............................. 2001-385491
Nov. 7, 2002 (JP) ............................. 2002-323253

(51) Int. Cl.
*C12Q 1/68* (2006.01)
(52) U.S. Cl. ........................................................ 435/6
(58) Field of Classification Search ............... 536/23.1, 536/23.5; 435/6
See application file for complete search history.

(56) References Cited

FOREIGN PATENT DOCUMENTS

| EP | 1 033 401 A2 | * | 6/2000 |
| WO | WO94/06936 | | 3/1994 |
| WO | 01/75067 | | 10/2001 |

OTHER PUBLICATIONS

GenBank® Accession No. AC027314 (Sep. 29, 2001).*
GenBank® Accession No. AC008570 (Sep. 29, 2001).*
GenBank® Accession No. AW196354 (Nov. 29, 1999).*
GenBank® Accession No. AA552939 (Aug. 11, 1997).*
Database EMBL 'Online! *Homo sapiens* Chromosome 5 Clone CTC-549a4., Oct. 1, 2001, DOE Joint Genomic Institute: "*Homosapiens* Chromosome 5 Clone CTC-549A4, complete sequence," retrieved from EBI, Database Accession No. AC008570.
Database EMBL 'Online! *Homo sapiens* Chromosome 5 Clone CTC-286c20, Oct. 1, 2001, DOE Joint Genome Institute: "*Homo sapiens* Chromosome 5 Clone CTC-286c20, complete sequence," retrieved from EBI, Database Accession No. AC027314.
Database EMBL 'Online! *Homo sapiens* Putative Nuclear Protein NSD1 mRNA, Dec. 13, 2001, Kurotaki, Harada, Yoshiura, Sugano, Niikawa, Matsumoto: "*Homo sapiens* Putative Nuclear Protein NSD1 mRNA complete cds," retrieved from EBI, Database Accession No. AF395588.
Imaizumi Kiyoshi et al, "Sotos Syndrome Associated with a De Novo Balanced Reciprocal Translocation t(5;8)(q35;q24.1)," American Journal of Medical Genetics, United States, vol. 107, No. 1, Jan. 1, 2002, pp. 58-60.
Database EMBL 'Online! Apr. 27, 2000, Whitehead Institute/MIT: "Human sts est156306, sequence tagged site," retrieved from EBI, Database Accession No. G26128.
Database EMBL 'Online! Aug. 18, 2000, Waterston, Genome Sequencing Center: "*Homo sapiens* chromosome 5 clone RP11-564G9, working draft sequence, 6 unordered pieces," retrieved from EBI, Database Accession No. AC023788.
Kurotaki N et al., "Molecular Characterization of NSD1, A Human Homologue of the Mouse Nsd1 Gene," Gene: An International Journal on Genes and Genomes, Elsevier Science Publishers, Barking, GB, vol. 279, No. 2, Nov. 28, 2001, pp. 197-204.
Kurotaki Naohiro et al, "Haploinsufficiency of NSD1 Causes Sotos Syndrome," Nature Genetics, vol. 30, No. 4, Apr. 2002, pp. 365-366.
Maroun C. et al., "Child with Sotos Phenotype and a 5:15 Translocation," American Journal of Medical Genetics, United States, vol. 50, No. 3, Apr. 15, 1994, pp. 291-293.
Database NCBI 'Online!, Dec. 12, 2001, Kurotaki, Matsumoto, Niikawa: "Molecular Characterization of NSD1 a Human Homologue of the Mouse NSD1 Gene," retrieved from NCB1, Database Accession No. AAL40694.
Wang, X. et al., the DDBJ/EMBL/GenBank databases [online]: submitted (Jul. 30, 2001) Accession No. AY049721.
Xin Wang et al., "Identification and Characterization of a Novel Androgen Receptor Coregulator ARA267-α in Prostate Cancer Cells," J. Biol. Chem., vol. 276, No. 44, (Nov. 2, 2001), pp. 40417-40423.

* cited by examiner

*Primary Examiner*—James Martinell
(74) *Attorney, Agent, or Firm*—Burr & Brown

(57) ABSTRACT

A nucleic acid is (a) a nucleic acid comprising a base sequence shown in base numbers 1–39726 of SEQ ID NO: 1, or (b) a nucleic acid wherein a part of the bases 1–39726 of SEQ ID NO: 1 is deleted, substituted or added, and having a homology of 80% for the base sequence. Also, a probe comprises the above nucleic acid, and a screening is carried out by using such a probe.

3 Claims, 4 Drawing Sheets
(4 of 4 Drawing Sheet(s) Filed in Color)

SEQUENCE LISTING

<160> NUMBER OF SEQ ID NOS: 8
<210> SEQ ID NO 1
<211> LENGTH: 39726
<212> TYPE: DNA
<213> ORGANISM: human chromosome

<400> SEQUENCE: 1

| | | | | | |
|---|---|---|---|---|---|
| tttgatgatg | ggttctgcct | ttgccatttc | agacacattt | tctataaatc | aagctagctg | 60 |
| aatctacagc | tctggagggt | tttttttttt | tttttttga | dacagaatct | cgctctgtca | 120 |
| cccaggctgg | agtgcactga | tgtgatcttg | ggtcactgca | acctctgcct | cccggcttca | 180 |
| agagattctc | ctacctaagc | ctgccaagta | gctgggatta | caggcgtgca | ccaccacgct | 240 |
| cagctaattt | ttgtagtttt | agtagagagg | ggatttcgcc | atattggcca | ggctggtttc | 300 |
| aaactcctga | cctcaagtga | tctgcccacc | tcggcctccc | aaagtgctgg | gattacaggc | 360 |
| gtgagccacc | agacctggcc | tctgggtttt | tttttttttt | tttgagacag | agccttacta | 420 |
| tgtcacccag | gctggagtgc | agtggcgcga | tctcagctca | ctgcaacctc | cgcctcccgg | 480 |
| gttcaagcga | ttcttctgtc | tcagcctccc | gagtagctgg | gactacaggt | gcccgccacc | 540 |
| acgcccagct | aattttgta | tttttagtag | agacagggtt | tcaccgtgtt | agccgggatg | 600 |
| gtcttgatct | cctgaccttg | tgatctgccc | gctttggcct | cccaaagtgc | tgggattaca | 660 |
| ggcgtgagcc | accgtgtccg | gccaacgccc | agctaatttt | ttgtagagat | gaggtttcgt | 720 |
| tgcccagtct | ggtcttcaac | tcctgcctc | cagtgatcca | cccacctcgg | catcccaaag | 780 |
| tgctgggatt | ataggcttca | gccaccacgc | ccagcccttt | tagtatttat | tgagcaacta | 840 |
| ctgggtacaa | actctttgtc | attcctccac | tagcaagagc | agtgatttca | tgagctgctt | 900 |
| ttcagccttt | gttttcatct | gtaaaatagg | atatcttctc | tttgaggggc | aacaagggt | 960 |
| aggtgtgggt | gggtgagcta | taaaccctaa | tcctcaccca | ggaggagtg | cagccacctt | 1020 |
| tctggccact | ggctggagac | ctcccccttt | ccccatactc | ctccttccac | tccctgatcc | 1080 |
| aagcactgcc | agaacccagc | attctctcac | tttctcttcc | tccgttttga | atcagtaggt | 1140 |
| tcagaagtgc | ttggcttgat | atgaagctgg | gggtgcatcc | aacaaaatca | gatgcctaga | 1200 |
| gaaggagcag | gattggggtg | ggagagagaa | gacagataat | tgggttgagg | aacctggggg | 1260 |
| catcctgaag | gaggtgccca | gtgggcagtt | gctttgtgct | gggcccaggg | ccaggttata | 1320 |
| cgtactttga | atattttatc | ttcatagcta | tcccatttgg | tgaggctcaa | agagcgaaaa | 1380 |
| tgacattcct | ggtaaatggc | cctgctgcag | tttgaatttg | tatccatctg | actccaggtc | 1440 |
| acgtaagctc | tttttgtttt | tgagacgag | tctcgcctg | tagcccaggc | tggagtgcaa | 1500 |
| tggcgggatc | tcagcttact | gcaacttcca | cctgccaggt | tcaagcgatt | ctcctgcctc | 1560 |
| agcctccctt | gtagctggga | ttacaggcac | gtgccaccac | gcccagctaa | tccttttgtat | 1620 |
| ctttagtaga | dacggggttt | caccatgttg | gccaggctgt | tctcgaaccc | ctgaccttgt | 1680 |
| gatccgccct | cctcggcctc | ccaaagtgct | gggattacag | gcatgagcca | ctgagcctgg | 1740 |
| tcataaggtc | tcttatactt | ttatttattt | atttattgga | gccagagtct | cactctgtca | 1800 |
| cccaggctga | agtgcaatgg | catgaacatg | gctcactgca | gcctccacat | cctgggctca | 1860 |
| agcgatcctc | ccacctcagc | ctgccaagta | gctgggacta | tgggtgcgaa | tcatacacca | 1920 |
| ccatgccagg | ataattgtt | tgtttgtttg | tttgttttt | taaatggagt | ttcgccttgt | 1980 |
| ggaccagggt | ggagtgaaat | ggcgcgatct | cagctcactg | caacctcagc | ctcttgggtt | 2040 |

-continued

| | | | | |
|---|---|---|---|---|
| caagcgattc | tcctgcctca | gccccccgaa | tagctgggat | tacaggtgtg tgccaccaca | 2100 |
| tccggctaat | tttgtatttt | tagtagagac | ggggtttcac | cacattggtc aggctggtct | 2160 |
| caaactcctg | acctcatgtg | acccacctgc | cttggcctcc | caaagtgctg ggattacaga | 2220 |
| tgtgagccac | agcgcctggc | ctacttttg | tattttttgt | agagacaagg tttagccata | 2280 |
| ttgcccaggc | tggtcttgaa | ctcctgggct | caagcgatcc | gtctgcctca gccttccaaa | 2340 |
| gtgctgggac | taaaggcgtg | caccactgta | cctggcctct | tatgctttgt aaagcattgt | 2400 |
| ctggcaccaa | aggctgtttg | ttcctcaaac | atcttgaatc | cttttgga ggatctgagt | 2460 |
| tttgtacaac | tcatttggtc | cgttattgaa | accacaattc | tgtctgatgg agacacaggc | 2520 |
| ttggagagga | gaggagggga | tagatcaggc | atcatgaaat | gtttctggag cactcactct | 2580 |
| gagcttcacg | gtctgggctt | gttcactgga | ggtcagagag | tatatgtcct tagtcttgtt | 2640 |
| ggaagtgact | gtccaactgg | atgagaccag | atttagaagc | cattagttac taccaggact | 2700 |
| cagggaaaaa | tggctgcctg | taggggtggg | aagactacca | ggaggaggag tcttctaaac | 2760 |
| tggatgaatg | gagtctgccc | aggggaaaag | gcagagtgac | tggcatgagc ataggctgga | 2820 |
| caggatgtgg | cttgtcctgg | cactgggcag | ttgggggaag | tgagcaggg agggcaggga | 2880 |
| ttagtggcca | ccataccaag | cttcagaagg | aggtttaaga | agaagaaaac ttaaaggtgg | 2940 |
| atgcttgagt | cctttcgggct | ggggctgggc | gtacaggctc | aggttagcga caggacctgg | 3000 |
| tatttggggc | aggaaggaga | ctgctggagg | gctgcctggt | ctcagatgtg gtcaggcctt | 3060 |
| ccttgatctt | aagttgaaaa | ctgattcaat | tttggggaaa | tccgtgggtg gggagaggaa | 3120 |
| ggaaacagct | cctagaccca | tcagaaggca | tggtcctggt | gttcaccagc tatgttcagg | 3180 |
| attaattacc | aaaggcctcc | atgcctctcc | caagacctaa | ctgtttagtc agaaggcaga | 3240 |
| tgctgttcct | gttcagtggg | aacaaggagc | tggaactagg | atgggagttt gtctctgggc | 3300 |
| aagtcatgct | tccttctag | aagatggga | taacaataat | acccatctca gaggagtaaa | 3360 |
| tgagtatcct | gcagggtagc | tggaacagag | gaggataagc | tacaactgtt attgtaacaa | 3420 |
| caggcagagc | ccttgctgga | gttgtgttc | taggggagga | accagtgtct tctgacaca | 3480 |
| gaagagtgag | ctttctactg | ctcagatgcc | atcacgtcat | tatcctcctc cctcaccttc | 3540 |
| catggctgct | tactgccttc | cagataaagc | ttcaactctt | taacttaacc aaccaagccc | 3600 |
| tgaagggtga | ggctctgtgt | ctgccccatc | cttggttgag | cctctttctg cactcattac | 3660 |
| ctctgccccg | gcacatacac | tagacatgct | tgttgtggtc | agttcctctg aagcctggtg | 3720 |
| tttctctgga | ctctgctgga | atctctgcct | cttcccttc | ttgcctggct attcctgaat | 3780 |
| atcctccagg | actctctctg | gatgttgctt | cctcaaggat | acccctgagt tagtttcaag | 3840 |
| ggcattctca | gcttctccag | cacccttggc | ttctctctca | gtactcagtt ctctgccttg | 3900 |
| ttattacctg | tctgcttttt | ccacaaggct | gtgacgggga | gccccaaaat atttatggaa | 3960 |
| ttaatgaatg | aaaaggggtg | gttctaagaa | aaagagatc | actgtacatt ggccaaatgt | 4020 |
| cccaacaggt | atctattata | tctcaccagg | gtaggaatta | tcagtaacca agatttacag | 4080 |
| atgaggaaac | tcagcccaag | gtagagtccc | tctgcctgtc | attcaaattt ctgggcacct | 4140 |
| gtgtgtaagc | accatgctgg | gcttttcaca | ggcagtatgt | gtagggtgga caggctgaga | 4200 |
| gcaagcacgt | gaggcccatc | ataccaggtg | agagttaagg | tgctgacacc ttgcatgagg | 4260 |
| gcttagtctc | ttggacctca | attcttcgta | gggctggtga | aggtcatag gaacgactgt | 4320 |
| atgtgaagtg | cccaggacag | tgtccagtac | actagtacag | acccagcaag tgtttactga | 4380 |
| ttcttatctc | agtcctaagg | atgggagtca | caggcccaga | aaaggtccct ggattgagac | 4440 |

```
aaccagccag aggagagctg agtgtacatc ccaggccccc accctacagg gacacagtcc    4500
tctcccttct gcccccactc aaggagtcag tgtccttgtg agaatctatg gcgctgtgga    4560
tcttctcaac ctagtgctgg cacacatgag atgcttggcc agggcctgcc agatggggag    4620
gctggagatg ggtcggctgt gattgagacc tctgtggcca agttttactc taagaggcag    4680
gtaaggccct caggggttat cccagagaag tctgagaggt tttccctggg gtcctggtct    4740
tctcccccag acctgtcagc aagcagttca tccccagctg ccaatctcct tttggccctc    4800
agtcttccag aggagctggg aagtgggaga gaggggttct gcagggcagt gttgttcaga    4860
ggtgagcttt ggaagaaact gttgtctcaa ccctattttc acaccatagc acctttattt    4920
aactgtcttt tcccgaggcc aggatctcat cttttgtttc cccagcactc agcacactgc    4980
ctggaatgca ggaaatggtt gctgaatgaa gcgatgaatt acatttcagc actcatcaag    5040
tgctcagcct ataactaagt ctgagtgtag gctgctaaca cttagacctt taccttacag    5100
aatcttcgca gccagtgctg tgcattggaa gttgcagatg gggaaactga ggctcaggac    5160
tgttaagtga ctagttcaag gcaggtctca ggccctcagg atggttagtg gcaaagtaaa    5220
ggactgggag gagcattgat gaattggggc aattggcaga ggagtaactg tcagtcaaaa    5280
tgattggctc aaattattag gtgtgaagaa ggaaccagtc agagcttgcc tgttgagtcg    5340
aattgcccag atgggattag cagggtgagt gaccctagca gaacaaagag ctggcccttg    5400
taggtataga ctcgactttt ctctggttgg tcccaacaca tagacaacta ccaacctgac    5460
tttgcacctg agaatcttca gggtacctca gactcttcaa cagaaggagc ctccctgagg    5520
tcacagccct ctcatcagtc ccgttccagt gggcacttt c cctctaacaa agcccacttg    5580
ctgtcttggc agggtctgca tccggcactt gcagacatgt gctaagggcc tgttgacttg    5640
ggagcctcca tcactggact gtgggccttg gagagcaaaa gggtaagagc atctcgagct    5700
ccacgcctgc tgggccagtc gctggctgaa ggcaggggaa ggatggagtt tagctggcca    5760
gcactaatgt cacacagggc aacgccaaaa atggcctttc tcccaggtgg gctcaaagtt    5820
aacagaaggc agtgagtaaa cagtccactg ggcaataac tatgcacatt tactaagcca    5880
tgggaagaat agtagtcacg tggccctcga gggcggtgcc ctcagcttga gatggagtta    5940
actccaaatc taatcacaga aggctttctg gaggaggcgg aattttatg gcggccggat    6000 ccggctttct ctgaacagcg agaaggcgct tagcgcccta gggaccaggt aactcctgag    6060
gtgagcttct tggtggggat caagcccagg gggcgacgga gtccgggctg ggggaagggc    6120
ccgaggggct ggagtcgcaa gttcaggccc agcttgggct ccctgtcccg cccttccgct    6180
gtcttggggg attggacgcc acgcggtcgt gctagattcg gtgctgcggg cccggtgcag    6240
gatgcaggcc gtgaggcccc aggccgaggg ctgcgccagc gggcttgtcc cggccagccg    6300
ggcggtcccg tgtcccggcg cagctccgct ggggtccaga tgcccggccc tcaggggcga    6360
ggcgcgcact cccccgggga accgggctgcg gagcaggcgg cccgctctgg gcggcggtgg    6420
cacgagaggg ccatctgcct gggtgccgag aactgcagcg tccgcggtgc gaggcgcggc    6480
ccgtcccgtc ccggccccca gccggccgcg cacgcacata cccacgccgg ccggcgcccg    6540
ctgcccgagc cccgtgcca ggcccagacc ttgactaggc gcgggaggcg gtgcagggac    6600
tagaggaccc cctcccccgg cgttcccctc gccccgcccg aggctgcgag gacccctggg    6660 ctcggggtg gtgagggagc ttcgtcccgg ctgggcccgg gctggggact cggcctccct    6720 gggcggggc cgcacggctg caggccgagg tgcggacgcg ctgtcaggct gcagcccggc    6780
```

-continued

| | |
|---|---|
| tcggtgccgg gggtgggctc agcgctgggg tcgcctggct tcgttccccc gcggaggcca | 6840 |
| cggccgggcg agcagtgccg gggcgggtaa cccgacccgg ctccccagag ccgctcaccc | 6900 |
| cgcacggccc ggcaagggga gggagaggga tgggggagg gggaagggaa gggtggtgg | 6960 |
| gtgaggggct gtgggcaccg cagggccgag tccccggccc gtctgcgctg ctgtagggcg | 7020 |
| gctgcccgcg gcacccggga cgatccagcc tctgcctcgc gggcgtcgag cctgagacag | 7080 |
| gagggagccc tggggctgca caggcttggc tcagggaggg agaccgagc tgctgcctcc | 7140 |
| attttgtttc ctgctcagct tggtctgtgg tggtggtggt ggtggtggtg tgggtttggg | 7200 |
| gtgcggccgg gtagggggtt cgcctgcggc gcgtctgct cggggcctga ggcctcgaag | 7260 |
| accccagccc aagccccag gtgagccctg cggcaggagg ggggttgcct tggcctcggg | 7320 |
| ccgaacccag cgggctgagg gcaggtgccc agtggatggg gagcctgggc tgtaacctaa | 7380 |
| gatggaggcc gggactgacg cgggcccgag cagggctggc gggacgatcg gacaggcctc | 7440 |
| agccgcgcca ggtgccgcct gggttgggt tcgagacgcg tagggtgcgg gagccgtgtg | 7500 |
| cggcccgagg ccagcgccgt gccccgaggt aggtgagggg atcggaatgc cacccacgac | 7560 |
| gcccgcaggc cccgacactc caaggaggcg cgcgaggccc ctggggagcc cgcctcaggc | 7620 |
| ccgcccggg cagccgggcc ggcccgtagg ccccggccgc gagcgggcgc gcagggggag | 7680 |
| gggaggggc ggcagcggca gctccgctga ttgggcggcg ctctcacaag cccgacttca | 7740 |
| cccgccctga accccgaaga gtgagagaag ggaacgcgcg cgctcggtgg gggaagggggt | 7800 |
| gcgcgcgcac tcggggccca gccgcacgcg ggccggcgcg aggcgctcgg tcgcacgcgc | 7860 |
| ggccgcgggg gcgcgcgcgg tgggggtgtg aggaggagga ggcggcggcg gaataggccg | 7920 |
| gggcaggtcg cgctcgctgc cttctcccct gaagagagac gcgggggag ggggtgcgg | 7980 |
| cgagcggccc cgctctctcc ccaccgctcc gctcgcaccc cagtgtaatg agggtcaccc | 8040 |
| cctcccccca gctggcccgg gagggggcgc ggggcacggt aactagtgcg ctgggtgggg | 8100 |
| cggcgggcag gcgcgaggag aagggaggga ggagggtggc cgggcgggga agatggtggt | 8160 |
| ggccgtaagg tgaggggctc gggggagggc caggcgcgat gcggggttgg tggccggcgg | 8220 |
| cgctgcagcc gccggcctcc tccccctccc cctcctccat cactaccagc cgggctcagg | 8280 |
| cctagctggc cgggctgccg cgaacttcct cccggcgcgg cccgtgcccc gccgccgcc | 8340 |
| tgcgaacacc tcggcctccg cctcccctca ggtagcaggc tgcggggcgc ggggccggct | 8400 |
| gccctcccgc agcaaacttt gcttgctgct gaatattgat gagagcgatc ggctcggctg | 8460 |
| ggaggtgctg ccgcggctgc gggaaggagc gcggcccggg caggcggcgg cggcgtcggc | 8520 |
| agcagccatg tttttcgagc tgtagcagct gctgctaccc tgactgggct tcgctggccg | 8580 |
| cctcggtttc tccctctgcc gggtccaggc ctcttcgccc tgcagctgcg gatccagcag | 8640 |
| gcctgcattc aggaaggcga gctctggggt gcagccgcct cggccggctc gcctgcggcc | 8700 |
| tgcgcaccgc cgctgcaaag gctccggcgc tggctgggcg caggtgcag cgctattgtg | 8760 |
| accgctgcgc cctagcgagc caggaagggg ggggtacctt tttgtgcagg gtccaggagc | 8820 |
| cccctcgga ccccgcagcc ttttgctttt gagagatcca gctgctcgac ccctggcgag | 8880 |
| ggagggggag gactagtcct gtttgagaat tgggaatttt gacgggcaga ggggttttaa | 8940 |
| ttttagttca tcccaagtgt ccaccagtct acagaggagg aaaaagagac gggctgtttc | 9000 |
| tatgtagcag gatcggccca gcttcgggaa aatggagttt tcagaggctc atcgaggcca | 9060 |
| tttttttcatc tccagtcggg ggaacttttt ctgcccatgg aagtgcagca gaaaggcata | 9120 |
| gaggccacta ggccttgaag tggctgccat tttaaagagt cgagtcagat ggcctattaa | 9180 |

-continued

| | |
|---|---|
| ctcagattaa ttgctgtgct tttggattcc aggttgatgc cggcccagga tggatcagac | 9240 |
| ctgtgaacta cccagaagaa attgtctgct gcccttttcc aatccagtga atttagatgc | 9300 |
| ccctgaagac aaggacagcc ctttcggtaa tggtcaatcc aattttttctg agccacttaa | 9360 |
| tgggtgtact atgcagttat cgactgtcag tggaacatcc caaaatgctt atggacaaga | 9420 |
| ttctccatct tgttacattc cactgcggag actacaggat ttggcctcca tgatcaatgt | 9480 |
| agagtattta aatgggtctg ctgatggatc agaatccttt caagaccctg aaaaaagtga | 9540 |
| ttcaagagct cagacgccaa ttgtttgcac ttccttgagt cctggtggtc ctacagcact | 9600 |
| tgctatgaaa caggaaccct cttgtaataa ctcccctgaa ctccaggtaa agtaacaaa | 9660 |
| gactatcaag aatggctttc tgcactttga aatttttact tgtgtggacg atgcagatgt | 9720 |
| agattctgaa atggacccag aacagccagt cacagaggat gagagtatag aggagatctt | 9780 |
| tgaggaaact cagaccaatg ccacctgcaa ttatgagact aaatcagaga atggtgtaaa | 9840 |
| agtggccatg ggaagtgaac aagacagcac accagagagt agacacggtg cagtcaaatc | 9900 |
| gccattcttg ccattagctc ctcagactga aacacagaaa aataagcaaa gaaatgaagt | 9960 |
| ggacggcagc aatgaaaaag cagcccttct cccagccccc ttttcactag agacacaaa | 10020 |
| cattacaata gaagagcaat taaactcaat aaatttatct tttcaggatg atccagattc | 10080 |
| cagtaccagt acattaggaa acatgctaga attacctgga acttcatcat catctacttc | 10140 |
| acaggaattg ccatttgtaa gcagtttttg gtacaactta aatatataca tatatgtata | 10200 |
| tatacaggcc acttaaaggg aaacttgtaa caaatttgtt tttggttgct tatcagttca | 10260 |
| cagctgaaat cctattgcta atcataagct ttgggcaaaa ttttactttg attttttaaat | 10320 |
| ttatctctgt tgtatgaatt tggttgtttt aagcttttttc caaataactc ttcattgaga | 10380 |
| gtaggctaat gcttttaaag gcatttgatt gagttcaggt ttaatttctc aagttggagg | 10440 |
| tatacatata tgattaaaaa aaaaaaaaa agatgggttt tggcctgcca gcaccatgag | 10500 |
| tgcaggtgaa ccaatttagt acttggagtc ctgttgctat atgtggcaga ttattttttt | 10560 |
| acttgatgac ttgactctta cttcaggttg aagggcattt tgaacacaga ttaaagtggc | 10620 |
| taagatgaag ttttcttgga cattgtcaaa atctaaatta ggctagtttt tctgaactac | 10680 |
| ctgtttttgaa ggtatagcat cctgtgcttt tgataactgc caccattagc tctttttttt | 10740 |
| ttttttgagg tggagtctca ctctgttgcc aggctggagt gcagtggttg atcactgcaa | 10800 |
| cctctgcctc ttgggttcaa gcaattctcc tgcctcaccc tcccgagtag ctgggattac | 10860 |
| tggtacccat caccacgccc ggctaatttt tgtatcacca ttagctcttg aagttttttct | 10920 |
| agttttgttt tgttttatttt tattttatttt taacagaacc ctaactaaga caaagtttta | 10980 |
| tatttattta ttgtttagag actggccttg tcatgttgcc caggctggcg tcgggactcc | 11040 |
| tgggctcatt cgatcctcct gcatcagcta gaactacagt agtttcagat ttgaagtgt | 11100 |
| gtatgtgtat gtgtgatatg tatatattcc gtgtgtatag aaatggagag tatcttattt | 11160 |
| gagttgttgt tttcagtaat gctgtcaagt attgttagag ggtgataaat gataacattt | 11220 |
| gttttttattt gagcttatga agaatttctt gactttctag ctaaatgatc agttcacttc | 11280 |
| tcttagcctc aattttattg cgtctaaatt ccagaagttc ttgattgcta taagattcct | 11340 |
| tcagctttaa atattaatat ttgatattga ttttgtttct gcccaaacac attgtttggt | 11400 |
| caccgccggt aatgttagca aagagaattt ttttttggcca acaaatgtct catacccacat | 11460 |
| tcagttttta taagaaaaac ttttatggta tgttgttatt ctgagttcat taaacattcg | 11520 |

-continued

```
ctttacctta tatccctgct gttctttaaa gttacagagg gagaatgtgg gtgtgtcact    11580
tttgtttctg ttgatttgta tcttaattat gccttggtac tccttggttt cttggcaatt    11640
gcagatttaa aaaaatttgc tttagtggtt atcttgagtc tgaattgtcc tacacattag    11700
ggtgggtagg ctgttttgaa aacctattgg cagctcagac aaatccttttt tcttgggttc    11760 acgttgaaat ttattttata tatatatcgt gtctttgttt ttgcacataa atttaaatct    11820
gagaatggag atagatgttt ctctagaagc atacaaatag aattgtaaac ctgtttctcg    11880
tcaaagagat gttagtggag tattggttct attaaaaaaa aaatgaaggc tgagtgtggt    11940
ggctcacacc tgtagtccca gcactttggg aggctgaggt ggacagatca cctgaggtca    12000
ggagtttgag accagtctgg ccaacatggt gaaactccgt ctctacaaaa attagccggg    12060
cgtgatggtg ggcaactgta atcccagcta ctcgagaggc tgaggcagga gaatcgcttg    12120
aacccaggag gcagaggttg cagtgagcca agattgcgcc attgcactcc atactgggaa    12180
ataagagtga aactctgtct caaaaaaaaa aacaacaaaa aaacaaacaa acaaacaaac    12240
aaaaaactga aaatattgga gcctttagat agtaggttac atgtctaaaa tgggagttag    12300
caaatgtata aatgtagaag ttttttttttc agggagaaat tgaaattgct caaagacttt    12360
atcaccttga agaagcaagt atgtagttta tttatttttt tgagacacag tcatgctgtc    12420
acccaggctg gagtgtagtg gcgcgatctc agctcacttc aaccacctcc tcctgggttc    12480
aagcgattct cccacctcag cctcccgagt agctgggact acaggtgtgc accaccatgc    12540
ctgactactt tttgtatttt tattagagac gaggtttcac catgtgggcc aggctggtct    12600
tgaactcctg acctcaggtg atccgcccac cttggcctcc caaagtgctg ggattacagg    12660
cgtgagccac cgtacccatc ccctaattta ttatttttagg aatttggttc aaagttgtga    12720
ttgaaatcta ttgcctttat ttttgccttt gatatttttta aactgaagac attttttttt    12780
ttgagacgaa gtttcactct tgttgcccag gctggagtgc aatggcatga tctcggctca    12840
ctgcaatctc cgccttctgg gttcaagcag ttcttcctgcc tcagccttct gagtagctgg    12900
gattacaggt gcgcaccacc accccagcta atttttgtat ttttagtaga tgggggttt    12960 taccatgttg gcccagctgg tctcgaactc ctgacctcag gtgatccacc cgcctcagcc    13020
tcccaaagtg ctgggattac aggtgtgagc cacggagccc ggcctcagac tgaggactta    13080
aaaagtgagg tcagggtggg catggtggct cacgcctgta atcccagcac tttgggaggc    13140
tgaggcgggt ggatcacctg agatgaggat ttcaagacca gcctggccaa catggcaaaa    13200
ccccgtctct actaaaaata caaaaaatta gctaggcatg gtggcaggag cctgtaatct    13260
cagctatttg ggaggctgag gcaggagaat cacttgaacc cgggaggctg aggttgcagt    13320
gagctgagat cgcccattg cactctagcc tgggcaacaa gagcgaaact ccctctcaag    13380
aaaaaaaaaa accatcctgg ccgacatggt gaaacccgt ctctactaaa aatacaaaaa    13440
ttagctgggc gtggtggcag gctcgggagg ttgaggcagg agaatcactt gaacccggga    13500
ggcggaggtt gcagtgagcc gagattgtgc cactgcactc cagccttgag acagagggag    13560
actccatctc aaaaaaaaaa aaaaaagcg gtcaatctta gaatgcaaag ttaggtaagc    13620
aatacagctt gagaaaagtg taattaaaaa taacttttct atgtagtcat gtgatattaa    13680
tgtattcaac ttgttcacag ttgatttaag ttattgatat agtaggtatt gttactatgc    13740
tgggaatttt agaaaatcct tagcaaattg ctatttgtct cttttttgtct gtaattttgg    13800 ctgggcttgg tggctaacac ctgtaattct agcaagttgg gaagccgaga caaaaggatt    13860
gcttggggcc cagagtttga aactagactg ggcaacatag tgagatcctg tctctacact    13920
```

```
cagttggttg tggtggtatg cctgtagtcc cagctactca ggaggctgag gcagtagtag   13980
gatcacttga ggccagaagt tgagactgc agtgagccat gatcatgcca ctgcattcca    14040
gcctaggcaa cagagcaaga tcctgtcaaa aaaaaaaaa aaggagaaaa ttctcttggc    14100
agtgggtaag agtagttatt agggttgtag atttcctgtc tggaattaga gaaagaaggg   14160
tcatattttc tgttattttg tgtatctacc tctaagtgga ctgtttgcct cttgtcacga   14220
attagtagcc tcttcagttt accatcatgt gctcttattt tctctgcata cagtgaagtg   14280
attgtcatta caatttataa tcctgacctg gtacttttat atttaattgg gctgatattt   14340
tctaattctt cccagtgtac aaaggtttta tgctttgttg ttgttgttga gacaggctag   14400
gtgctttgga tgtggagaat taaatgagca tggcattttc agaggatact tgttggagat   14460
tgcttgggta ggatggatgt agtcagctaa tggggcctag aaattcagac tgaagcattt   14520
ggtattgatg tgatgggaac tggcagccct tgagagattt tagctgagaa gtgatgtaaa   14580
atctgtttgg aagactttga gtagaggaga ttagaggcaa ggttaggatg tagggtatgt   14640
tgcaatagta attaagactt aagaatcggc ccagtggcat gtacctgtag tcctagctac   14700
tctggaggcc gaggcaggag gatcacttga ggctgcaatt agctgtgatt gtgcctgtga   14760
atagccactg cactccaacc taggcaatat aatgagattc tgtctcttaa aaaaaaaatg   14820
agcacagtga gtactctaaa gaaagggggt aaatctaaaa gattatttca aagggagaaa   14880
attggcagct ttttgggggc tacctgatct ggaggcagat tggagtctgg atttgaggaa   14940
tggagagaga tgaggcagat gatgtctaag gcttatagtt ttgctgcctg agacaaaaat   15000
gattcctcag aggttccttc ctcttctcta cccatcatcc cacaattttc tactccctcc   15060
ttagctatct tggaagaaaa ttgatctctt cacacctgag gttctgctct ctctccgatt   15120
ccctcctggc tgggtgacct ttttgtttg ttttgtttt tgttttgaga cagagtctca   15180
ctctgtcacc caggctggag tgcagtgggg cgatctcggc tcactgcaac ctctgcctcc   15240
caggttcaag caattctctg cctcagcctc tggagtagct gggattacag gcgcccgcca   15300
ccgcaaccag ctaattttta tattttagt agagacgggg tttcaccatc ttggccaggc   15360
tggtcttgaa ctcctgacct cgtgatccac ccgccttggc ctcccaaagt gctgggatta   15420
caggcgtgag ccaccgcgcg cagccttttt ttttttttt tttttttttt ttttaagatg   15480
aattcttgct ctgttgccca ggctggagtg cagtggtgtg accttagccc acggcaacct   15540
ccatctcctg ggttcaagag attcttgtgc ctcagcctcc caagtagctg ggattgcagg   15600
cgccctccac catgcttggc taattttgt attttagca gagagaggtt tcaccatgtt   15660 ggccaggct gtctcgaacc cctgacctca gtgatccac ctgcttcagt cttttcaaagt   15720 gctggaatta caggtgtgag ccaccacgac ctgcatacca cttctcaaac agtcctttt   15780 tgcgtccttg ttctcttttt cttcctcttt ctctgcagtc tcattcactt tcattgattc   15840
tgctgctact ccactctatg aaactctctt ctgaactgac ttcaaaccaa caaattctac   15900
ttgtcaacta agctgctcct ctaccttgtg ttatattcac ctaaaatgta atattatttc   15960
cttttttatt tttcctttgg acagggtctt tctctgtcac ccaggctgta gtgcagtggt   16020
gccatctcgg ctcactgcaa cctctgcctt ctgggttcaa gtgattctcc tgcctcagcc   16080
tcctaagtag ctgggactac aggcgcccac caccatgcct ggctaatttt tgtatttta   16140 gtagagacag ggttttgcca tgttggccat gctggtctca aactcctgac ctcaagtgat   16200
acgcctgcct ctgcttccca aagtgctggg attacaggca tgagccactg cgcccagcct   16260
```

-continued

```
attattttca ttttgaaccc atctctttta ttgccaaaca cgcatttact tctgtgttca   16320
tgatgacatc attatcctat tcatctcaaa gctggaaacc ttgcagtcaa tcatttaaat   16380
gattaaaata catttgagta cctcttgagc caggcactgc cagtataata aaaaataaaa   16440
aaattaaaaa aaggaaagag atagtttgct tttaaggaac ttcactgtgt ggcaaaaact   16500
agtgtaaaca atgacaatac agaatactaa gtggtctggt aggtgttatg tatgcagtac   16560
tttgggagtg tggaggaagg catgcctaga ataatcaggg aggacttcac agagtggtta   16620
tttatagttt aagcagagac ataccagtaa gagggaatag catatgcaag tggccagaaa   16680
tccttggcta gctatctggg aggagtgggg ttgtcaggga taaaggtat aaagataggc    16740
ttatatgccg tgctgtatag ttgaatgttt ttactattac aaaattttac agatgccctc   16800
agtttctccc tttattcatt tttctatgac atctttattg ttggtcttca tttagtcttt   16860
ccttccagtc tatcctgtgt aaaattactt cctacttcca aaatgagaaa tactgggtct   16920
ctacttaaat ttgtaaccta aatgcctcac acctcattt ctgaacaaat aaagcccaaa    16980
ttcagtgtcc tttttgatag gatcctgtcc tgacctttcc aaatctgatg ctagagcctt   17040
gtgtaccctg agttcagcca aactgaactc ttaatggtcc cttgctccat actctcccct   17100
tgctcatgcc tttattctcc tggtctgatt catctttgca tcttaacagt gtatagcatg   17160
gtgccttctt tttactgggg acatatcgag ttaatgaatg aatgatgcta ttacagaggt   17220
acagtttggg aaggggagtg agtacatttt agaaaggtga taagtggatt gtcagccttc   17280
atcattttca atggaccaaa ttactaaaac tttacaggtt ggttggtttt ttttcttttt   17340
tcatttcctc atgtactcaa tttctaaggc ttttgaatt tgagcttcct aatatctcat    17400
gcattaattt ttttctccat tctcaacttt cactctttta attaaggata ataattttt    17460
tttttgagat ggagtcttgc tctgttgcac aggttcgagg gcagtggtgc gatcttggct   17520
cactgcaatc tccgtctgcc gtgttcaagc aattctcctg cctcagcctc ctgagtagct   17580
gggattacag gtgcatgcca ccacgcctgg ctaattttg tattttttaga agagatgggg    17640
tttcaccacg ttggttaagc tggtcttgaa ctcctgacct tatggtccgc ctgcctcagc   17700
ctcccaaagt gctgggatta caggcatgag ccactgagcc tggccaagga taataaatta   17760
taatggtttt aggttggaca tctctgactg catactgcac tgtgtttact ggaagaagtc   17820
ccttaatgtc tctaaggccc atttcctcag ttctaaatta cggctagtac cttcattgga   17880
gggttgttaa gtctatgata caagataact ttttttttt tttttttttg agacagagtc    17940
tctatcgccc aggctggagt gcaaaatggc acgatcttgg ctcactgcaa cctccacctc   18000
atgggttcaa gttgattctc ctgcctcagc ctcccaagta gcttggatta taggcatgcg   18060
ccaccatgcc cgactaattt tgtgttttta gtagagatgg ggttcaccac gttggccagg   18120
ctggtcgaac tcctgacctc aggtgatcga cccacctcgg cctcccaaag ttgctaggat   18180
tacaggtgtg agccatctct cctggccatg atacaagata atttatatga agtaatacac   18240
tgctggttct gaagtaggtg tgcagtaagt gatgcctact gctgcatgcc aagagtcaaa   18300
tgtatatttg aaagagttgt gaatttcaag aaagatattt ttgagttttt ttttttttct   18360
ttctgagaca gggtcttgta ctgtttccca ggctagagtg cagtggcctg atcttggctc   18420
ctggctgggc ccaagtgatc caccgccctc agccttccaa cgtattggga ttacgggaat   18480
gagccactgc atttggctaa gttttttgttt ttttttctc tattttttcca aacttatttg   18540
attagtaaga taaagacatt aactgctgtt gacagtttcc atttttaatt agtaatcagg   18600
agcatttgtt gtattttttgt ttgataatca gaataattta atttgtgcaa taggatcaat   18660
```

-continued

```
agctttctgt attccaactg ttaagtggtg taagtttatt acattgttgc tttttgcagg    18720
ttgtcctttg ttctagatag aaatgtttaa tttattcttc ctggttttca ggggagccca    18780
ttgaaaggag atccagtctc tgaaatttag tggtaggata taacaattg aacagttact    18840
tttgaatcta atttaaataa tctcaattgt agccttttaa agcaattcct atgaaccttt    18900
ttgaatttag aaaagtaata cttggccggg cgcggtggtt cacatctata atcccagcac    18960
tttgggaggc tgagggggtg gattatctga ggtcaggagt tcaagaccag cctggccaac    19020
gtagtgaaac cctgtctcta ctgaaaatac aaaaaaaaat tagctgggtg tggtggcacg    19080
tgcctgtagt cccagctact caggaggctg atgcaggagg atcgcttgaa cccaggaggc    19140
agaggttgca gtaagctggg attgtgccac tgcactccag cctgggtgac agagtgagac    19200
tttgtctcaa aaaaaaaaa aaaaagtca aacttaaaaa tggaatataa aaatctcttg    19260
attttttgtca gttttcatat actccctcat ttacactctt aatattctat tagaaattgt    19320
ctcttctctc tacacacccc ttttttttccc ttttggttaa tatgttaaga catcttttca    19380
tatgagcatg taacatgtaa caagattttt tttttttttt ttggacagtg tctcgctctg    19440
ttgctcaggc tggagtctag tagtatgatc acaactcact gcagtttaga cctcctgtgt    19500
taaagtgatt ctcctacttt agcctcatga gtagttggga ctacaggccc atgccaccac    19560
gcctggctaa ttaaagaaaa aattatttgg tagagacagg gtcttgctat gttgcccagg    19620
ctggtcttga atttctggct tcaggcaatt ctcctactct gcatgagcca cctcagccgc    19680
gaatattttc ttattatgaa attttgtttt agataaatgt tgattcacat gcagttgtaa    19740
caaattccat ggccaggctg gcgtggtgg ctcacgcctg taatcccagc actttgggag    19800
gctgaggtgg atcacctgag gttgggagtc caagaccagc ctgaccaaca tggagaaacc    19860
ccgtctctac taaaaataca aaattagcca ggcgtgatgg tgcgtgcttg taatcccagc    19920
tacttgggag gctgaggcag aagaatcact tgaacccggg aggcggaggt tgtagtgagc    19980
caagatcgtg ccattgcact ccagcctggg ctagaagagc gaaactccat ctcaaaaaaa    20040
aaaaaaaaa aatcaggaaa ttccatgggc taggcacagt gacttatgcc tgtaatccca    20100
gcgttttgga aggctgaggt tggaggattg cttgagccca ggagtttgag gctacagtga    20160
acactgactg tgccactgca ctccagcctg ggtgaccctg tctcttaaaa aaaaaaaga    20220
atacagagag gtcccttgta tattttgcct ggttttgcaa tggtaatatt ttgcaaaaaa    20280
tatctaatac cacacaacca gaatattgat gttgatgtac ttcaccaatc gttttttttt    20340
tttttttttg agtcggagtc tccatctgat gcccaggcta gagtgcagtg gctcaatctc    20400
ggctcactgc aacctccacc tcctgggttc aagcaattct cctgcctcag cctcctgagt    20460
agctgggact acaggcgtgt gctatgacgc ccagctagtt tttgtatttt tagtagagac    20520
ggtgtttcac cgtgttatcc agggtggtct caatctcccg accttgtgat ccgcccgcct    20580
cagcctccca aagtgttggg attacaggct tgagccaccg cgtccagcca gtcttactta    20640
ggcattgacg ttcatgtaat ttatccatct tattcagatg tccttaaatt ttatctttt    20700
ccttaaaaga aatctgtatt tctatcagga cattctggat gtccccagtt ttactggtag    20760
tctttcattg tgtgtatatt aagttctttg ttttatcac ctgtataggt tagtatatcc    20820
atgactcccg tcaactttct aaatgttcgc tgggtgcagt ggctcatgcc tgtaatccca    20880
gcactttggg aggctgaggc ggctggatca cctgaggtca gtagttcgag accagtctgg    20940
ccaacatggt gaaaccccgt gtctactaaa aataaaaaaa aaattagctg gatatggtgg    21000
```

```
gtcatgcctg taatcctagc tactcgggag gctgaggttg gagaatcgct tgaacccagg    21060
aggcggaagt tgcagtgagc tgagatcgcg ccgctgcact ctagcctggg tgacagagta    21120
tgtctctgtc tcaaaaaaaa aaaaaagtt gctaaacatt tctaatacca taaggatccc     21180
tgctgttgcc agccgtttta aaactacatc catcgtcttc ttggcaacct ccatctctt     21240 tttcgtatgt gacagcgtct tgctctgccg cccaggctgg agtgcagtag ttgcatctca    21300
gctcactgca ccctctgtgt cccaggctta agcgatcctc ccacctcagc ctcctgatta    21360
gctgcgacta caggcacttg ccaccatgcc ccactaattt ttgtatgttt ttgtagagat    21420
ggggttttac catgttgctc aagctcgtct tgaactcgtg agctcaagca atccgcctgc    21480
cttggcctcc caaatggctg ggattacagg caggagccac catgcctggc ctagcccctc    21540
catctctagc ctttgtcagt tactaaactt ttttttcctga agttttgtca tttcacaaat   21600
gttagataaa catgagtcat acagtatgca gccttttggg attgtctttt tttcccttag    21660
cataatttcc aggggattca tctaagttgt tgactaaatc aatagttgtt ttttttgttt    21720 gtttttttt tgagacggag tttcactctt gtggaccagg ctggagtgca atggcatgat     21780
cttggctcac tgcaacctcc gcctcccagg ttcaagcgat tctcctgcct cagcctcctg    21840
agcagttggg attataggcc cctgccacca cacccagcta attttttgtat ttttagtaga   21900 gatgggtttt caccatgttg gtcagggtag tcttgaactc ctggcctcaa gtgatctacc    21960
tgcattggcc tcccaaagtg ctgggattac aggtgtgagc cactgcgcac ggccctagtt    22020
tttttccttt tatcactaag taatattcca tgatacaaat ataccatggt ttgcttgacc    22080
gttcacctgt tgaaggacat ctggggcaat gctagctttt ggtaattaag gtaaaagtac    22140
tatttatgtt catttatggg gttttgtgtg actgtaagtt ttcacttctc tgggataaat    22200
accagtagaa caattgcagt attatatggt aatggcatgt taagttttt tttttcctg     22260 agagggagtt tcgatcttgt tgcccaggct ggagtgcaat tgcgcgatct tggctcgctg    22320
caacctctgc ctcctgggtt caagcgattg tcctttctca gcctcgcatg tagctgggat    22380
tataggtgtc aaccaccaca cccagctcat ttttgtattt ttagtagaga tggggtttca    22440
ctgtgtttgc caggctggtc ccaaactctt gaccccaggt gatccaccct cctcagcctc    22500
ccaaagtgct gggattacag gcgtgagcca cggcgccccg ccaatgttca gttgtttttt    22560 tgttttttg agacaatctc tctctgtcac ccaggctgga gggcagtggc gcgatcctgg    22620
ctcactgcaa cctctgcctc ccggattcaa gcgattatcc cgcctcaggc tcctgagtag   22680
ctgggaccac aggtgcacac caccacacca ggctaatttt tttattttta gtagagacgg    22740
ggtttcacca tgttgggtca ggctggtctc gaactcctga cctcaggtga tccacccacc    22800
tcggcctccc gaagtgctgg gattacaggt gtgagccacc acgcctggcc caatgttcag   22860
ttttataaga aactaccaag ctgtttccc tagtgtctgt accatttaca ttctcactag     22920
cagtatatga gtgatccagt ttctttatt ttttgttttt tgagacggag tctcgccctg     22980
ttgcccaggc tgaagtgcag tggcacgatc tcggctcact gcaacctctg cttcccggct    23040
tcaagtgatt ctcctgcatc agcctcccaa gtagctggga ttacaggcat gtgcaccatg    23100
cctggctaat ttttgtatt tttagtagag atagggtttc accatgttgg ccaggctggt     23160
ctcgaactcc tgacctcagg taatccaccc atcttggctt cccaaagtcc tgggatttca    23220
ggcatgagcc attgcacctg ccgagtgct tcagtttcta tgcatcctca ccagcatttg     23280
gtgtggtcac tatttaatt ttagccattc gtgtagatat gtagtaatgt ctcatctcat     23340
tatgttttgt tttttttt gagacggaat gttgctcttg ttgcccagac tggagtgcag      23400
```

-continued

```
tgatgccatc tcggttcact gcaacctcca cctgctgagt tcaagcaatt ctcgtgcgtc   23460
agcctctgga gtagctggga ttataggtgt gcatcaccat gcctggctaa ttttttgtatt  23520 tttttagtaga catggggttt caccacgttg gccaggctgt tcttgaactc ctgacctcag  23580
gtgagctgcc cacctcggcc tcccaaagtg ctgggattac agttttgtat ggtggattcc   23640
atgcagagag agttttttct gtagtctaga ttagcagtcc ccagccttt  tggcaccagg   23700 gaccaaattc ctgggaaaca gttttccac  aggtgggagt gggatggttt ggggatgaaa   23760
cttttccacc ttagattatc acgcattagt tagaatctca taagaagcgc gcaacctaga   23820
tcccttgcat ttgcagttca aatagggtt catgatcctc tgagaatcta atgccacccc    23880
tgatgtgaca ggagtgggag ctcaggcgat aatgctccct tgtctgctgt tcacctcctg   23940
ctatgcagcc cggttcctaa caggctgaga ggaccagtac cattctgtgg cctgggcgtt   24000
ggggacccct gttctagatg atccacattc ttttaaatgc ctatatacaa accatacttt   24060 cttttatttct tttcttttt  tgagacagtc ttactctgtc acccaggcta gagtgcaatt   24120
gcgtgatctt ggcacactgc aacctctgcc tcccaagttc aagtgattct cctgcctcag   24180
cctcccgagt agtaggact  acaggtgtgt cccaccatgc ctggctaatt ttttatattt   24240 gtattttta atttttattt atttatttat tttttgaga tggagtctcg ctctgtcacg     24300
caagctggaa tgcaatggca cgatctcggc tcactgcaac ctccgcctcc cgagctcaag   24360
cgattctcct gcctcagcct cctgtgtagc tgggattaca ggcacccgcc acgacgcctg   24420
gcttttttgt attttgtag agacaggttt tcactgtgtt gtccgttctg gtctcaaact    24480
cctgagttca gggaatccac cgccttggcc tcccaaagtg ctgggattac agtcgtgagc   24540
caccgcgccc tgccacaaac catactttga aaacgttgct tccatttta gataatttgt    24600 taggaaacca ataaaatcat acatacttgt gattttccct tagtaaaaca caaattttag   24660 tgtttttgc  tgttattatt aatacttcta aagttccttt cacattgcta gtgaccttat   24720
ataaaatacc ataatgctct tctagcaatt gctggaaaga taaaatctat tttagagaat   24780
gaacaattat attttcacat tagattaaat taaaagtaat tactggttat gtgatattcc   24840
ctcacatacc agagtgagtc tgaaggtagt cttctttgt  aaattatgag gctatatttc   24900
ctgtgttatc tctgatttct cttgatgctg taattggagt tgttgggtct ccctggtgaa   24960
agtaggtgat gtgcaagttg tgtctatacc cagtgaaaat aacagacatt aatgctacac   25020
taatttgtca ttggaatttt acattcaaaa gcatttcttt ttaaaaatat gattgtaaat   25080
tggtaattta tagttgtata taccaaaggc atttctttaa cgttatagtt ggttcaactg   25140
aaaatacgtt aagtctgttt ttataattag tatattgagg aacagcactt ccatcgtgtc   25200
acaatatatt aagaattgcc agcagggcac ggtggctcac gcctataatc ccagcacttt   25260
gggaggccta gcgcggagga tcacctgaag ccaggagtcg agaccagcct ggctaacgtg   25320
gccaaacccc tatctactaa aaatacaaaa attagccagg tgtgatggcg ggtgcctgta   25380
gtcccagcta ctcgggaggc tgaggcagga gaatccagaa ttgaattgaa cccaggagac   25440
ggaggttgca gtgagccaag attgtgccat tgcactccag cctggacaac acagcgagac   25500
tcagtctttt ttattttat ttttatttt  gagacggagt ttcgctcttg ttgcccaggc    25560
tggagtgcaa tggcacagtc tcggctccct gcaacttctg cctcccgggt tcaagcgatt   25620
cacctacctc agcctcccga ctagctggga ttacaggcat gtgccaccac gcccggctaa   25680 ttttttgtatt tttagtagag atgggatttc tccatgttgg tcagacttgt ctcggactcc   25740
```

```
caacctctgg tgatctgccc gcctcggctt cccaaagtgc tgggattaca ggcatgagcc   25800
accgtgcgtg tcctttttt tttttttatc ttttgagaca gggtctcact ctgttggcta   25860
ggctggagtg cagtgatgca gtcacaactc actgcagcct caacctccca gtctcaagca   25920
atacccccac ctctgcccct tgagtaggc tgggactaca ggtgtgtgcc ttcataccta    25980
gctaattttt tttgttttgt tttttgagac agtcttgccc catcgcccag gctggagtgc   26040
agtggtgcca tctcggctca ctgaaagctc cgcctcccgg ttcacgcca ttctcctgcc    26100 tcagcctccc gagtaactgg gaccacaggt gcccgccacc acaccggct aatttttgt     26160 attttagta gagacggggt tcaccatgt tagccaggat agtctcgttc tcctgacctc      26220
atgatccgcc tgccttggcc tcccaaagtg ctgggattac aggtgtgagc cactgcacct   26280
ggccatgcca agctaatttt tgtatttttt tgtagggatg ggatggcact atgttcccta   26340
ggctagtctt taattcttgg gttcaagtgg tcctcctgcc tcggcctccc aaagtgttgg   26400
gattacaggt gtgagccact gtgccgagcc aggttgtgtg tgtgtgtatg tatgtatgta   26460
tgtatgtatg tatgtatgta tgtatgtttg tatatattta tatttatttt tttggaactg   26520
catctcactt tcatccaggc ccgaatgcag tgacatgatc tcagctcact gcaacttctg   26580
cctcctgggt tcaagcgatt cttttttt tttttttt ttgagacgga gtctccctct       26640
gtcgccaggt tcactgcaag ctctggctcc cgggttcacg ccattctcct gcctcagcct   26700
cccaagtagc tgggactaca gatgcccacc agcatgcctg gctaattttt tgtattttta   26760
gtagagatgg ggtttcactg gggtttcacc atgttagcca ggatggtctt gatctcctga   26820
ccttgtgatc cgcccgcctc tgcttcccaa agtgctggga ttacaggcgt gagccactgc   26880
gcctggccat ttctttttt ttttggcaa gtgattcttg tgcctcagcc tcccgagtag    26940
ctgaaattat aggcgtgtgc cctcaacgcc tgggtaattt ttgtatttt agtagagaca   27000 gggtttcacc atgttggaca ggctggtctc aaactcctgg cctcaagtga tccaccctcc   27060
tcagcctccc aaagtgctgg gataacagct gtgagccacc gtgcccttcc caggttttat   27120
atttattctt ttttccttt aaattatgtt tttatttagg tattgtacgt aaagtgcttt    27180
tctaacagag ctttggggca gaagtgttag ggcaggtcat taaaccactg aaattagttc   27240
tttggaggag aagataattg ttagagttgt aagtgaagtc ttgatagata ccttatcaat   27300
ttcatagtaa tgtctgtgga atttcttttt ctgtttttt tttttttaat tatttcttga    27360
ggattaactg ctgatagtgg aatatcatat atatagttgg ctcttgatgt acttatttct   27420
ggatggcttt ccaaaaggat tttaccattt tacacacagt tctaaatagt atatgaattt   27480
agcatttgtc ccacacttag atagcactga tttttttt tattaagtgg gtgcaaaatg    27540
ctactacaag attgctttaa ttactacagt tttattgatg aaaatgattt ctacttgttt   27600
actgtttgta ttttttcta ggagttttgt gtctatattc tttgctgatg tatcttttttg   27660 gatttaatgt tttatacata ttaaatttct gtctcattgg atataaatat ttcccaatc    27720 tggttttcat tttagttaat gatttctgt agttgtatag tcaaagtttc atttattata   27780
tagctagatc tgtgttttcg agtgatttat tgattcaaag cttattgtgc ttctagatat   27840
ttgataaact gactttagac tcttgtaaaa atttgaagaa ctcatatcta ctacagtctt   27900
actgatttaa tagggttttt aatatccagt actatgctaa taatttttat agtgttttta   27960
cgacaatttt ttgagaacat aagttttag agctgtggat ggaatgtttt ctgctctatc    28020
agttatccct tctgcgtaac agaccccta agtgtagcagc ttagaggagt aaatatttat   28080
tatctcacat tttgtaagga atcatggagt ggcttagctg gatggtgctg gctcagtctc   28140
```

```
tctaatgaat ttacagtcaa gatgtctgcc agggctgcgg tctctgaagg ctgtaggatc   28200
cctgtccaag acggctcact catatggatg ctagctcttt gtatgaggcc tgttctttcc   28260
cacttgcact tctccatagg cctgcttact gtatggtagc tggcttttcc cggagtgagt   28320
gatccaagag acagggacag accaagcagg aagatgcagt aacttttat gatgtgtatt    28380 ctattggctg gccacacata ccaagcagat agggaaggga ttacacaaag gcatgaatac   28440
catcaggctg ggataattgg gggccagctt ggaatctggc taccatatcc aaccaaataa   28500
gaaattaata gttttaatta aaggaaaagg attatattaa atagacattc gttagttttt   28560
acttttaagc tgacccaatc attttcaga ttgaagtttt gaatagatat atgattaaaa    28620
aatacatgaa aagttaacca gtgaagtgac ctctgtgcca tgtttgctca ggtaacgcac   28680
ctccaattct tgtgctttcc cggagaccac cttttttaag agaaaggtag tggactgtgc   28740
acacttggtc ttcctttttc acataatggt gtatgttgaa atctttccat tttagagcat   28800
agctttccct ttttaatttt attattatta ttattttga gacagagtct ccctctgtcg    28860
ccccagctgg aatgcaatgg tgcgatctcg gctcactgca acctccagct cctgggttca   28920
agtgattctc ctgcctcagc cacctgagta gctgggatta cagtcgcctg ccaccatgct   28980
cggctaattt ttgtattttt agtagcgacg gggtttcacc atgttggcca ggctggtctc   29040
gaactcctga cctcaggtta tccacctacc tcagcctccc aaagtgctgg gattacaggc   29100
gtgaggcacc gtgcccggca attttttttt tttgagtcag agtcttgttc tgttgcccaa   29160
gttggagtgc agtggtttga tctcggctca ctgcaacctg tacctcctgg gttcaagtga   29220
ttctcctgcc tcagcctccc gagtagctgg gactacaggc atgccccacc atgcttggct   29280
aattttgtat tttagtagag actaggtttc tccatgttgg tcaggtcgt gtcaaactcc     29340 ctacctcagg ggatccgccc accttggcct cccaaagtgc tgggattata cgttagcc     29400 accgcgcctg gcctaatttt tgtattttca gtagaaattt ttgtatttca ctgtattggt    29460
caggctggtc tggaactcct gagctcaggt gatccacccg cctcggcctc ccaaagtgct   29520
gggataacag gagtgagcca ctaggtgtga cctaattttt gtattttag tagagatggg    29580 atttcaccat gtcggctaag ctggtctcga actcctgacc tcaggtgatc tgcctgcctt   29640
ggcctcccaa tgtgctggga ttataggcat aagccaccgc actggctttt ttttttttt    29700 tttttttaaa cctggatggt tttattttgc atgaatgtat agatatttcc tgttcataca   29760
ttctgaaagt gaacaactgt atatatgcaa tttatttta ttcttattta tttatttgtt    29820
tattttttga gaccagagtc tcactctgtc gcccaggcta gagtgcaatg acacaatctc   29880
ggttcactgc aacctctgcc tcctgggtta agcaattctt ctgcctcagc ttccccagta   29940
gctgggatta caggtgtccg ctaattttg tattttaca aaatacaccc aggtaatttt     30000
ttgtaatttt ggtagagaca ggtttcacca tgtcggccag ctggtctcg aactcctgac    30060 ctcaggtgat atgcccgact cagcctccca aagtgctggg attacaggtg tgagccactg   30120
cgtctggcct gcatggggat tcttaatgaa gattaattat tgtagttgag ggggaaaagg   30180
aataataaat atttattgga ccctaaatac cttcgaatat ggaataccct aggtattcta   30240
gggcatttag ggaccaataa atatttattc ctccgtactc ttccctcgct cttttcagat   30300
tttttttttt tttttttttt ttttgagatg gagtcttgct ctgtctccag gctggagtgc   30360
agtggcgcga tcttggctca ctgcaacctc tgcctcctgg gttgaagtga ttctcttgcc   30420
tcagcctcct gagtggctgg gactacaggt gcataccact atgcccagct aattttgta    30480
```

```
tttttttgtag agacaggctt tcaccatgtt ggccaggatg gtctcgttct ttagacctcg   30540
tgatctgtct tcctcagcct cccaaagtgt tggaattaca ggcgtaagcc tccgccgggc   30600
cttttttaga ttttttaagag aattttttgtt aaagcatgaa cttaaaaaat cagacttggc   30660
ttggagcggt ggctcatggc ctctagtccc aggactttgg gtggctgagg caagtggatt   30720
gcttgagccc aggagttcaa gacctgcctt ggcaataata tcaagacccc ctcttcatga   30780
aaaacaatca agctaatact tgatactatt ttacataaga attttttata gtatgtcatg   30840
ttttaatgta tattggttat atagttgcaa atttaaaggc atggtggtgg ctcatacctg   30900
taatcccagc actttgggag gctggggcgg gcagatcttc tgaggtcagg agttcaagac   30960
cagcctggcc aacatggtgg aaccccgtct taggctgagg caggagaata gcttgtgccc   31020
aggaggcaga ggttgctttg agctgagatc gcaccacggc attccagcct ggaggacaga   31080
gcgagactct gtctctaaat aaataaataa ataaataaat gtatactaac tgcattagca   31140
agactccgtc tctaaataaa taagtgaata aataaatgta tactaattgc attttaaaaa   31200
tcaaagtata ggccgggtac ggtggctcac aactgtaatc ctagcacttt tggaggctga   31260
ggtggatgga tcacctgagg tcaggagttt gagaccagcc tgaccaacat ggtgaaactt   31320
tgtctctact aaaaatacaa aattagctgg tgtggtggcg catggctgta atcccagcta   31380
ctcgggaggc tgaggtagga gaattgcttg aacctgagag gtggaggttg tggtgagcgg   31440
agatcgtgct gttgcactcc agcctgggca acaagagcga aacttcgtct ccaagaaaaa   31500
aaaaatatat aattcacata agataaaatt caccctcttt ggccaggcgc agtggctcat   31560
gcctgtaatc ccagcacttt gggaggtaga ggtgggcaga tcacttgagg tcaggagtt   31620 tgagaccagc ctggccaaca tggtgaaacc ccatctctac taaaaataca aaaattagcc   31680
cggtgtggtg gcatacacct gtaatccacc tactcaggac gctgagtctg cactcagtcc   31740
ctgggctaca gggtgaaact gtatctcaaa aataaagaat aaaatgcagc tacttaaagg   31800
gtgtagagtt gaacaactgt taccactgtc taattccaga accttcatc accccaaaag   31860 aaaacccatt cccagcagtc atttcccatt aagtctcctc tagcccctca caaccactaa   31920
tctaattcat gtttctatgt atttgcctat tctaggcgtt tcatacaaat acagtcatat   31980
aatttgtggc ctttcgtgtc tgacttgttt aacttagcat aatgttttaa ggcccattta   32040
tgttgttgta tgtatgcata cttcattcca ttttactgct gaatattgct ttgtactgat   32100
gccacttttt gtttgtcttt tcatcacttg acggacattt tgtttcttcc actttgtggc   32160
tgttacaggc agtgctactg tgaaaatttg tattaaagtt ttagcgtgaa tatatgttttt   32220 cagttctctt gggaaaatac ctagaagtgg tattgtcgga tcatagggtc attctatgtt   32280
tagcattttg aggaacagcc agactgtttt acatagtggt tgcaccgttt tacagtccta   32340
ctttagccta tatgggttct aatttctttc tttctttctt tctttctttc tttctttctt   32400
tctttctttc tttctttctt tcttttcttt cttttctttc ttttctttct tttctttctt   32460
tctttctttc tttttttaga acagagtctc cctctgtagc ccaggctgga gtgcagtggc   32520
atggtcttgg ctcactgcag cctccgcctc tcgggttcaa gcaattctct gcctcagcct   32580
cccaagtagc ttggactaca ggcgcccgcc accacgcctg gctaatgttt gtattttttgg   32640 tagtgacagg gtttcaccac attggccagg ttggtcttga actcctgacc tcaggtgatt   32700
cacccacctc ggcctcccaa agtgccgaga ttacaggcat gagccactgc atccgggcgt   32760
gggttctaaa ttcttaatat tctcatcaac atttattgct gtcttttttaa ttttagcctg   32820 taatcccagc tactagggcg actgaggtgg tagcatcgct tgagcccagg aagctgaggc   32880
```

```
tgcagtgagc caagattgca ccactgcact ccaggctagg tgatgaagtg agacttcatc   32940
tcaaaaaaaa aaaaaaggaa gtaatggcaa aaactggaat tattttgcac caacttaaat   33000
atttagatct ttaataccct tggaaagttt tttatatata gtttgtgtgt gtgtgtgtgt   33060
atatatacac acatatatat atacacacac atatatacac acatatatat gaatgatttt   33120
atatatatat atatatatat atatgaatga tatatatata tatatatgaa tgaatgaatg   33180
agatggagtc tcactctgtc acccaggcag gagtgcagtg gtgccatttt ggcttatggc   33240
agcctccgcc tccggggttc aagtgattct tgtacctcag cctcccgagt tgctgggatt   33300
acaggcactc gccaccatgc ccggattttt tgtcttaatt catgaaggat gaattaagtc   33360
tgcagttgtt cttttttccct ttttctttcc agttttttttt tttgtttgtt tgtttgtttt   33420
tgagacacag tctcactcgg ttgtccaggc tggagtgcgg tggcagtatc ttggctccct   33480
gtaacccatc tccctggttc aagcgattcc ggtgcctcag cttcccaagt agctaggatt   33540
acaggtgtgt gacaccacac ctggttaatt tttgtatttt tagtagagac gaggtttcac   33600
cgcattggtt aggttggtct caaaactcct gacctcaggt gaaccgccca cctaagcctt   33660
ccaaagtgct gagattacat gcatgagcca ccaagtctgg cctaagtctg aattttttttt   33720 tttttttttt tgagacggag tttcgctctt gttgcccagg ctggagtgca atggcgcgat   33780
cttggctaac cgcaacctcc gcctcccacg ttcaagcaat tctgcctcag cctcccgagt   33840
agctgggatt gcaggcatat accaccacgc ctggctaatt ttgtattttt gttagagatg   33900
gggtttctcc gtgttgagac tggtctcgaa ctcctgacct caggtgatcc gcctgcctcg   33960
gcctcccaaa gtgctgggat tacaggtgtg aaccactgca cccggccgaa tatatttttt   34020 tttttttttaa atggagtctc gctctgtggc ccaggctgga atgcagcggt gtgatcttag   34080
ctcactgcaa cctctgcctc cctggctcaa gcgattctcc tgcttcagcc tcctgagtac   34140
ctgggaccac aggtgtgcac caccatgcct gaataatttt tttgtgtttt tgtagagatg   34200
gagtttcacc atgttggcca ggctgatctc gaactactga cctcaggtga tgtgcctgcc   34260
tccgccttcc caagtgctgg gattacaggc atgagctact gtacccggct aagtgtacag   34320
tgttcttgtg atgtctttgt ctggtgttgg tatcagggta atactgtctt caagattacc   34380
cttgaatgag ctttacttca ttttttaatg tgtttttttt tcttttctttt tgttttttgt   34440 ttttgagaca gagtttcact ctgtcgcaca ggctggaatc cacactctag gctcgctgca   34500
gcctccacct cccaggttca agagattctc ctgtgtcagc ctcttgagta gctggggtta   34560
caggcacgtg ccacgacgcc cggctgattt ttttgtattt ttagtagtga cgggctttca   34620
ccatgttggc caggctggtc tcgaactcct gacatcaagt gacctgcctt cctcagcctc   34680
ccaaagtgtt gggattacag gagtgagcca ctgtgccccg cctgcaatta cttcttaagt   34740
tctcaattaa aagagagttt atcaaggact ttttttggta attttgcatt ttgaaaattg   34800
ctaacattaa ctgggacagc cctttttattt atttatttgt cactcagttg ttttttttgag   34860 ttgcctacta tgtcccaggc actggtaaga taggagtatc attgtacctg aggcagggca   34920
acatgtgctt gcttgagagg agcatgatct aggattataa ggactgcaac ctcccccttcc   34980 caggttgaag cagttctcat gcctcagcct cccaagtagc tgggactaca gccatgagcc   35040
accacgccca gctaattttt gtgtttttag tagagatgag gtttccccat gttggccagg   35100
ctagtctcaa cttctggacc tcaggtgatc tgcccacttc agcctcccaa agtgctgaaa   35160
ttacaggagt aatttttattc tcccaaagct gctgctttgg gagaataaaa agttgagtat   35220
```

```
gggccaggca tgggggctga tgcctgtgat cgcagcactt taggagactg aggtgggagt    35280
ctagcttgag cccagtagtt tgagacaagc ctggggaaca tagggagatc cggcctctac    35340
aaaaaaaata aattagctgg gtggagtggc atgtgcctgt ggtcccagct acttgggtgg    35400
ttgaggtggg aagatatctg agctcaggag ttccaggctg cagtgagctc tgattatgca    35460
ctccagcctg ggtgacagag tgagatgctg tctcaaaaaa aaaaattcag tgtggcgtga    35520
ttaggctggg agggtggggc aggaagggat gacattggag gggtaggcaa ggtgtagata    35580
gacctttccc tatattctcc tattttttaaa aaattttttt ctaaatagag atagggtctt    35640
actattttgc ccaggctggg tctcaaactc ctgggctcaa gtaatccttc catctaggcc    35700
tctattttt gtgcaaacga ttgaaattat attttttta cctgaatttt tcctgtgaac    35760
attgggttat ttataaacct gttttctgtt tctttctttc tttttttttt ttttttgtttt    35820
tgttttttga gatagagtcc agcctggagt gctgtggcat gatcttggca cacttgcaac    35880
ctctgcctcc tgggttcagg tgattctcct cctctagcct cctccacgcc tggctaatat    35940
ttgtattttt agtagagatg gggtttcacc catgttggcc gggctgttct tgaactcctg    36000
gtttcaacag atccacctgc ctcagcctgc caaagtgctg agattacagg tgtgagccac    36060
tgttctaggc acttgtttct gtttcttaat tttggctgct actcagtggg aaaaagcaca    36120
gattgaatct aattgaggcc gggcgctgtg gctcactcct gtaatttcag cactttggga    36180
ggctgaggtg gcagatcac ctgagatcca gagttcgaga ctagcctggc caacatgggg    36240
aaacctcatc tctactaaaa acacaaaaat tagttgggcg tggtggctca tggctgtagt    36300
cccagctact cgggaggctg aggcatgaga attgcttcaa cccgggaggt ggaggttgca    36360
gtgagctgag atcaggacac tgccctccag gttgggcaag agagtgagac tcggtcttaa    36420
aaaaaaaaaa aaatctagtt gaaaatgtc atcgggtctt tccaaatttt tactaggaat    36480
ttgttaaaat taaccaggct ggaagtcatt atagtttgtt tgtttgtttg tttgtttgag    36540
atgggggtct cactctgtca cgcaggctgg agttcagtgg taggatctcg gctcactgca    36600
acctctgcat cccagattca agcgatcctc tcacctctgc ctcatgagta gttggaacca    36660
caggcatgtg tcaccatgct tttgtagaga cagggttttct ttcgcccctgt tggctaggct    36720
ggtctcaaac ttgtgagctc aagcgatccg cccaccttgg cctcccaaag tgctgggatt    36780
acaggcatga gttaccttgc cttgcccatt atagcttttt tgaggctggg tcttactctc    36840
tgtcatgcag gctggactgc agtggtgtga tctaagctca ctgcctcctg ggctcaagca    36900
gtcctccac ctcagcctcc tgagtagctg gcacaggcgc tacctcaccc atctaatttt    36960
ttatttttt tagagatggg gttttgccat gtttgcccag gctggtctag aattcatgag    37020
ctcaagtgat ctacctgcct cggcctccca atgtgctggg attacagaca tgagccacta    37080
tgttcagcca tacctggcta attttttaaaa aatgttttca agagacaggg tctccctgtg    37140
ttgcccaggt tggtctcaag ttcctgggat tactgctggc cttcaaaagt aaatgtgaaa    37200
taattagtta atttctccct cagttgacaa ataatgccaa aagtgataaa gattaatgaa    37260
atgtctcttt tttttttttt ttttttgagac ggagtctcgt tctgttgcca agtctggaat    37320
gcagtggcac gatctcggct cactgcaacg tccacctact gggttcaagt gattctcctg    37380
cctcagcctc ccgagtagct gggactacag gcacgcatca ccatgcccgg ctaatttttg    37440
tattttttagt agagacgggg tttcactatg ttggccaggc tggtcttgaa ctcctgacct    37500
catgatccac ccaccttggc ctcccaaagt gctgggatta caggcatgag ccaccgcgcc    37560
cagccatgaa atttcttacg tagaaaggca gcttgggatt gtagaaagaa tgtaggcttt    37620
```

```
ggagttggac aggcctccat ttgagaccat acttgagtcc cgtgcttgcc ttagacaaag    37680
aacctctcaa ccttagtttt taatctataa ggtgttttga aaattaattc ctagttcagt    37740
acatggcaca tggtaggtac ctgctgctat ccataattct cttagttaat atattcggtg    37800
ccacatgcca ggcagccagg atctgtacta agcacctaat aagtattatc tcatttaatc    37860
ctcaaaagaa ccccacctga gttgctagac agccattatt tcagggttac acattaggaa    37920
attgaagctt agagagattt aagtggttag ccaagtgatg gtgctggtat tccaactaag    37980
gtcatctgct ttcagagcat ttactttctg ttaggctgcc tctcctgttg caaagtacta    38040
agaacacaac tacataatgt atttttagtg gattcttgtc tttttgtaaa tagaaggtta    38100
aaatgagagg aatttttttt ttgtttggga gacgtggtct cgctctgatg agagctagaa    38160
atttgattac ttgtatttct ggtctgcata aaaatttggc ctaaaaacat caatagaaag    38220
gcaagtgtca tctgcaaatc tgtcccatcc tgttcttcac aggaaaatgt aaccttttt     38280 tttttttttt tctttttttg agatggagtc tagctctgtt gcccaagctg gagtgcaatg    38340
gcatggtttc ccgctcactg caacctctgc cttctgggtt ctagcagttc tcctgcctca    38400
gcctcctgag tagctgggat tacaggcgcc tgccaccatg cctggctaat ttttgtattt    38460
ttagtagaga cagggtttca ccatgttggc caggctggtc tttaactcct gacctcaggt    38520
gatccgcctg cctcggcctc ccaaagtgct gggatcacag gtgtgagcca ctgcgcccgg    38580
gctcaaaatg taacgtctgt ctagtatgag gatttattc cttgtctgac ttctgagttg     38640
taatcgttta ttaacaatca cattgtaagt ttatctatga agtaataaaa tgttctttct    38700
gtatattata ctggaaatga atgcttcatt caaaaaatag ttttatcttg ggaaggtagc    38760 cacttttaa aaattgaggt aaaacggcca ggcacggtgg ctcacgccca taattccagc     38820
actttgggag gccaaggtgg gtggagatca cctgaggtca gaagttcaag accagcctgg    38880
ccaatatggt gaaactccat ctctactaaa atacaaaaat tagaccggca tggtggcagg    38940
tgcctgtaat cccagctact caggaagctg aggcaggaga atcgcttgaa cccaggaggt    39000
ggaggttaca gtgagccgag atcctgccgc tgcattgaag cctgggtgag aagagcgaaa    39060
ctctgtctca ttaaaaaaaa aaaaaagag gtaaaattta ataacttaa ggctgattgt      39120 attggcttac acttgtaatt ccagcatttt gggagaccaa ggcaggagga tcacttgaac    39180
tcagaagttt gagaccagcc tggtcaacat agggaaacct catctccaca aaaaataaaa    39240
aataaaatat aaaaacttca aaattaaata agttacagtt caccattgta accatttttat    39300 tttatcctat ttattttgag acagtcttgt tttgtcaccc aggctggagt acagtggtgg    39360
gatcacagct cactacagcc tccaccttcc aggttcaagt gattcttctg cctcagcctc    39420
tgtaactggg attacaggtg cttgccacca cccctgcta atttttgtat tttgattaga    39480
gacagggttt caccatgttg gcccgattgg tctcgaactc ctgagctcaa gtgatctgcc    39540
tgtcttggcc tcccaaaatg agccaccgtg cctgtcccct tagtctactt taaaattcaa    39600 tttgccttt ttttaaattg taagaattcc ttatatattt tggatattaa atccttaact    39660
agggatatga ttcgcaaatt ttttcccc attctgtttc tgtaggctct ttgacattct     39720
tttct                                                              39726
```

<210> SEQ ID NO 2  
<211> LENGTH: 8511  
<212> TYPE: DNA  
<213> ORGANISM: human chromosome

<400> SEQUENCE: 2

```
ggtgcggcga gcggccccgc tctctcccca ccgctccgct cgcacccag tgtaatgagg    60
gtcacccct cccccagct ggcccgggag ggggcgcggg gcacggttga tgccggccca    120
ggatggatca gacctgtgaa ctacccagaa gaaattgtct gctgcccttt tccaatccag    180
tgaatttaga tgccctgaa gacaaggaca gcccttcgg taatggtcaa tccaattttt    240
ctgagccact taatgggtgt actatgcagt tatcgactgt cagtgaaca tcccaaaatg    300
cttatggaca agattctcca tcttgttaca ttccactgcg gagactacag gatttggcct    360
ccatgatcaa tgtagagtat ttaaatgggt ctgctgatgg atcagaatcc tttcaagacc    420
ctgaaaaaag tgattcaaga gctcagacgc caattgtttg cacttccttg agtcctggtg    480
gtcctacagc acttgctatg aaacaggaac cctcttgtaa taactcccct gaactccagg    540
taaaagtaac aaagactatc aagaatggct ttctgcactt tgagaatttt acttgtgtgg    600
acgatgcaga tgtagattct gaaatggacc cagaacagcc agtcacagag gatgagagta    660
tagaggagat ctttgaggaa actcagacca atgccacctg caattatgag actaaatcag    720
agaatggtgt aaaagtggcc atgggaagtg aacaagacag cacaccagag agtagacacg    780
gtgcagtcaa atcgccattc ttgccattag ctcctcagac tgaaacacag aaaaataagc    840
aaagaaatga agtggacggc agcaatgaaa agcagcccct tctcccagcc cccttttcac    900
taggagacac aaacattaca atagaagagc aattaaactc aataaattta tcttttcagg    960
atgatccaga ttccagtacc agtacattag gaaacatgct agaattacct ggaacttcat   1020
catcatctac ttcacaggaa ttgccatttt gtcaacctaa gaaaaagtct acgccactga   1080
agtatgaagt tggagatctc atctgggcaa aattcaagag acgcccatgg tggcccctgca   1140
ggatttgttc tgatccgttg attaacacac attcaaaaat gaaagtttcc aaccggaggc   1200
cctatcggca gtactacgtg gaggcttttg gagatccttc tgagagagcc tgggtggctg   1260
gaaaagcaat cgtcatgttt gaaggcagac atcaattcga agagctacct gtccttagga   1320
gaagagggaa acagaaagaa aaaggatata ggcataaggt tcctcagaaa attttgagta   1380
aatgggaagc cagtgttgga cttgcagaac agtatgatgt tcccaagggg tcaaagaacc   1440
gaaaatgtat tcctggttca atcaagttgg acagtgaaga agatatgcca tttgaagact   1500
gcacaaatga tcctgagtca gaacatgacc tgttgcttaa tggctgtttg aaatcactgg   1560
cttttgattc tgaacattct gcagatgaga aggaaaagcc ttgcgctaaa tctcgagcca   1620
gaaagagctc tgataatcca aaaaggacta gtgtgaaaaa gggccacata caatttgaag   1680
cacataaaga tgaacggagg ggaaagattc cagagaacct tggcctaaac tttatctctg   1740
gggatatatc tgatacgcag gcctctaatg aactttccag gatagcaaat agcctcacag   1800
ggtccaacac tgccccagga agttttctgt tttcttcctg tggaaaaaac actgcaaaga   1860
aagaatttga gacttcaaat ggtgactctt tattgggctt gcctgagggt gctttgatct   1920
caaagtgttc tcgagagaag aataaacccc aacgaagcct ggtgtgtggt tcaaaagtga   1980
agctctgcta tattggagca ggtgatgagg aaaagcgaag tgattccatt agtatctgta   2040
ccacttctga tgatggaagc agtgacctgg atcccataga acacagctca gagtctgata   2100
acagtgtcct tgaaattcca gatgctttcg atagaacaga gaacatgtta tctatgcaga   2160
aaaatgaaaa gataaagtat tctaggtttg ctgccacaaa cactagggta aaagcaaaac   2220
agaagcctct cattagtaac tcacatacag accacttaat gggttgtact aagagtgcag   2280
agcctggaac cgagacgtct caggttaatc tctctgatct gaaggcatct actcttgttc   2340
```

-continued

```
acaaacccca gtcagatttt acaaatgatg ctctctctcc aaaattcaac ctgtcatcaa    2400
gcatatccag tgagaactcg ttaataaagg gtggggcagc aaatcaagct ctattacatt    2460
cgaaaagcaa acagcccaag ttccgaagta taaagtgcaa acacaaagaa aatccagtta    2520
tggcagaacc cccagttata aatgaggagt gcagtttgaa atgctgctct tctgatacca    2580
aaggctctcc tttggccagc atttctaaaa gtgggaaagt ggatggtcta aaactactga    2640
acaatatgca tgagaaaacc agggattcaa gtgacataga aacagcagtg gtgaaacatg    2700
ttttatccga gttgaaggaa ctctcttaca gatccttagg tgaggatgtc agtgactctg    2760
gaacatcaaa gccatcaaaa ccattactttt tctcttctgc ttctagtcag aatcacatac    2820
ctattgaacc agactacaaa ttcagtacat tgctaatgat gttgaaagat atgcatgata    2880
gtaagacgaa ggagcagcgg ttgatgactg ctcaaaacct ggtctcttac cggagtcctg    2940
gtcgtgggga ctgttctact aatagtcctg taggagtctc taaggttttg gtttcaggag    3000
gctccacaca caattcagag aaaaagggag atggcactca gaactccgcc aatcctagcc    3060
ctagtggggg tgactctgca ttatctggcg agttgtctgc ttccctacct ggcttactgt    3120
ccgacaagag agacctccct gcttctggta aaagtcgttc agactgtgtt actaggcgca    3180
actgtggacg atcaaagcct tcatccaaat tgcgagatgc ttttttcagcc caaatggtaa    3240 agaacacagt gaaccgtaaa gccttaaaga ccgagcgcaa aagaaaactg aatcagcttc    3300
caagtgtgac tcttgatgct gtactgcagg gagaccgaga acgtggaggt tcattgagag    3360
gtggggcaga agatcctagt aaagaggatc cccttcagat aatgggccac ttaacaagtg    3420
aagatggtga ccatttttct gatgtgcatt tcgatagcaa ggttaagcaa tctgatcctg    3480
gtaaaatttc tgaaaaagga ctctcttttg aaaacgaaa aggcccagag ctggactctg    3540
taatgaacag tgagaatgat gaactcaatg gtgtaaatca agtggtgcct aaaaagcggt    3600
ggcagcgttt aaaccaaagg cgcactaaac ctcgtaagcg catgaacaga tttaaagaga    3660
aagaaaactc tgagtgtgcc tttagggtct tacttcctag tgaccctgtg caggaggggc    3720
gggatgagtt tccagagcat agaactcctt cagcaagcat acttgaggaa ccactgacag    3780
agcaaaatca tgctgactgc ttagattcag ctgggccacg gttaaatgtt tgtgataaat    3840
ccagtgccag cattggtgac atggaaaagg agccaggaat tcccagttg acaccacagg    3900 ctgagctccc tgaaccagct gtgcggtcag agaagaaacg ccttaggaag ccaagcaagt    3960
ggcttttgga atatacagaa gaatatgatc agatatttgc tcctaagaaa aaacaaaaga    4020
aggtacagga gcaggtgcac aaggtaagtt cccgctgtga agaggaaagc cttctagccc    4080
gaggtcgatc tagtgctcag aacaagcagg tggacgagaa ttctttgatt tcaaccaaag    4140
aagagcctcc agttcttgaa agggaggctc cgttttttgga gggcccttg gctcagtcag    4200 aacttggagg tggacatgct gagttgccgc agctgacctt gtctgtgcct gtggctccgg    4260
aagtctctcc acggcctgcc cttgagtctg aggaattgct agttaaaacg ccaggaaatt    4320
atgaaagtaa acgtcaaaga aaaccaacta agaaacttct tgaatccaat gatttagacc    4380
ctggatttat gcccaagaag ggggaccttg gcctttctaa aaagtgctat gaagctggtc    4440
acctggagaa tggcataact gaatcttgtg ccacatctta ttcaaagat tttggtggag    4500 gcactaccaa gatatttgac aagccaagga agcgaaaacg acagaggcat gctgcagcca    4560
agatgcagtg taaaaaagtg aaaaatgatg actcgtcaaa agagattcca ggctcagagg    4620
gagaactaat gcctcacagg acggccacaa gccccaagga gactgttgag gaaggtgtag    4680
```

```
aacacgatcc cgggatgcct gcctctaaaa aaatgcaggg tgaacgcggt ggaggagctg    4740
cactcaagga gaatgtctgt cagaattgtg aaaaattggg tgagctgctg ttatgtgagg    4800
ctcagtgctg tggggctttc cacctggagt gccttggatt gactgagatg ccaagaggaa    4860
aatttatctg caatgaatgt cgcacaggaa tccatacctg ttttgtatgt aagcagagtg    4920
gggaagatgt taaaaggtgc cttctaccct tgtgtggaaa gttttaccat gaagagtgtg    4980
tccagaagta cccacccact gttatgcaga acaagggctt ccggtgctcc ctccacatct    5040
gtataacctg tcatgctgct aatccagcca atgtttctgc atctaaaggt cggctgatgc    5100
gctgtgtccg ctgtcctgtg gcataccacg ccaatgactt tgcctggct gctgggtcaa     5160
agatccttgc atctaatagt atcatctgcc ctaatcactt taccctagg cggggctgcc     5220
gaaatcatga gcatgttaat gttagctggt gctttgtgtg ctcagaagga ggcagccttc    5280
tgtgctgtga ttcttgccct gctgcttttc atcgtgaatg cctgaacatt gatatccctg    5340
aaggaaactg gtattgcaac gactgtaaag caggcaaaaa gccacactac agggagattg    5400
tctgggtaaa agttggacga tacaggtggt ggccagctga gatctgccat cctcgagctg    5460
ttccttccaa cattgataag atgagacatg atgtgggaga gttcccagtc ctctttttg      5520
gatctaatga ctatttgtgg actcaccaag cccgagtctt cccttacatg gagggtgacg    5580
tgagcagcaa ggataagatg ggcaaaggag tggatgggac atataaaaaa gctcttcagg    5640
aagctgcagc aaggtttgag gaattaaagg cccaaaaaga gctaagacag ctgcaggaag    5700
accgaaagaa tgacaagaag ccaccacctt ataaacatat aaaggtaaac cgtcctattg    5760
gcagggtaca gatcttcact gcagacttat ctgaaatacc ccgttgcaac tgtaaagcta    5820
ctgatgagaa cccctgtggg atagactctg aatgcatcaa ccgcatgctg ctctatgagt    5880
gccacccac agtgtgtcct gccggagggc gctgtcaaaa ccagtgcttt tccaagcgcc     5940
aatatccaga ggttgaaatt ttccgcacat tacagcgggg ttggggtcta cggacaaaaa    6000
cagatattaa aaagggtgaa tttgtgaatg agtatgtggg tgagcttata gatgaagaag    6060
aatgcagagc tcgaattcgc tatgctcaag aacatgatat cactaatttc tatatgctca    6120
ccctagacaa agaccgaatc attgatgctg gtcccaaagg aaactatgct cggttcatga    6180
atcattgctg ccagcccaac tgtgaaacac agaagtggtc tgtgaatgga gatacccgtg    6240
taggcctttt tgcactaagt gacattaaag caggcactga acttaccttc aactacaacc    6300
tagaatgtct tgggaatgga aagactgttt gcaaatgtgg agccccgaac tgcagtggct    6360
tcttgggtgt aaggccaaag aatcaaccca ttgccacgga agaaaagtca agaaaattca    6420
agaagaagca acagggaaag cgcaggaccc agggtgaaat cacaaaggag cgagaagatg    6480
agtgttttag ttgtgggat gctggccagc tcgtctcctg caagaaacca ggctgcccaa     6540
aagtttacca cgcagactgt ctcaatctga ccaagcgacc agcagggaaa tgggaatgtc    6600
cgtggcatca gtgtgacatc tgcgggaagg aagcagcctc cttctgtgag atgtgcccca    6660
gctcctttg taagcagcat cgagaaggga tgctttcat ttccaaactg gatgggcgtc      6720
tgtcttgtac tgagcatgac ccctgtgggc caatcctct ggaacctggg gagatccgtg     6780
agtatgtgcc tccccagta ccgctgcctc cagggccaag cactcacctg gcagagcaat     6840
caacaggaat ggctgctcag gcacccaaaa tgtcagataa acctcctgct gacaccaacc    6900
agatgctgtc gctctccaaa aaagctctgg cagggacttg tcagaggcca ctgctacctg    6960
aaagacctct tgagagaact gactccaggc cccagccttt agataaggtc agagacctcg    7020
ctgggtcagg gaccaaatcc caatccttgg tttccagcca gaggccactg acaggccac    7080
```

-continued

```
cagcagtggc aggaccaaga ccccagctaa gcgacaaacc ctctccagtg accagcccaa    7140
gctcctcacc ctcagtcagg tcccaaccac tggaaagacc tctggggacg gctgacccaa    7200
ggctggataa atccataggt gctgccagcc caaggcccca gtcactggag aaaacctcag    7260
ttcccactgg cctgagactt ccgccgccag acagactgct cattactagc agtcccaaac    7320 cccagcttc agacaggcct actgacaaac cccatgcctc tttgtcccag agactcccac    7380
ctcctgagaa agtactatca gctgtggtcc agaccttgt agctaaagaa aaagcactga    7440
ggcctgtgga ccagaatact cagtcaaaaa atagagctgc tttggtgatg gatctcatag    7500
acctaactcc tcgccagaag gagcgggcag cttcacctca tcaggtcaca ccacaggctg    7560
atgagaagat gccagtgttg gagtcaagtt catggcctgc cagcaaaggt ctggggcata    7620
tgccgagagc tgttgagaaa ggctgtgtgt cagatcctct tcagacatct gggaaagcag    7680 cagcccttc agaggacccc tggcaagctg ttaaatcact cacccaggcc agacttcttt    7740
ctcagcctcc tgccaaggcc tttttatatg agccaacaac tcaggcctca ggaagagctt    7800
ctgcaggggc tgagcagacc ccaggggcctc ttagccaatc cccgggcctg gtgaagcagg    7860
cgaagcagat ggtcggaggc cagcaactac ctgcacttgc cgccaagagt gggcaatctt    7920
ttaggtctct cgggaaggcc ccagcctccc tccccactga agaaaagaag ttggtaacca    7980
cagagcaaag tccctgggcc ctgggaaaag cctcatcacg ggcagggctc tggcccatag    8040
tggctggaca gacactggca cagtcttgct ggtctgctgg gagcacacag acattggcac    8100
agacttgctg gtctcttgga agagggcaag accccaaacc agagcaaaat acacttccag    8160
ctcttaacca ggctccttcc agtcacaagt gtgcagaatc agaacagaag tagtaccaat    8220
caatgtcaca tgaacaaaca agctgccccc agggtaccat ttggggaggg gaaatctttt    8280
ctttctttcc cccttaaaaa aaaacacatc tgccccgaac actttccac tgttattctt    8340 tcctcatatc ccaacactca gaactcttgt gacattagcc agtgggggct tatggttgtg    8400
tgaaccatgt atgaaaatcc agtgggcccc aaccaaggag acagacagac ttgggtctct    8460
ttcccccaac ttttccacat ggtcatcgtg aaataaaaag tccactctgg a             8511
```

<210> SEQ ID NO 3
<211> LENGTH: 309
<212> TYPE: PRT
<213> ORGANISM: human chromosome

<400> SEQUENCE: 3

```
Met Asp Gln Thr Cys Glu Leu Pro Arg Arg Asn Cys Leu Leu Pro Phe
 1               5                  10                  15

Ser Asn Pro Val Asn Leu Asp Ala Pro Glu Asp Lys Asp Ser Pro Phe
            20                  25                  30

Gly Asn Gly Gln Ser Asn Phe Ser Glu Pro Leu Asn Gly Cys Thr Met
        35                  40                  45

Gln Leu Ser Thr Val Ser Gly Thr Ser Gln Asn Ala Tyr Gly Gln Asp
    50                  55                  60

Ser Pro Ser Cys Tyr Ile Pro Leu Arg Arg Leu Gln Asp Leu Ala Ser
65                  70                  75                  80

Met Ile Asn Val Glu Tyr Leu Asn Gly Ser Ala Asp Gly Ser Glu Ser
                85                  90                  95

Phe Gln Asp Pro Glu Lys Ser Asp Ser Arg Ala Gln Thr Pro Ile Val
            100                 105                 110

Cys Thr Ser Leu Ser Pro Gly Gly Pro Thr Ala Leu Ala Met Lys Gln
```

-continued

```
            115                 120                 125

Glu Pro Ser Cys Asn Asn Ser Pro Glu Leu Gln Val Lys Val Thr Lys
        130                 135                 140

Thr Ile Lys Asn Gly Phe Leu His Phe Glu Asn Phe Thr Cys Val Asp
145                 150                 155                 160

Asp Ala Asp Val Asp Ser Glu Met Asp Pro Glu Gln Pro Val Thr Glu
                165                 170                 175

Asp Glu Ser Ile Glu Glu Ile Phe Glu Thr Gln Thr Asn Ala Thr
                180                 185                 190

Cys Asn Tyr Glu Thr Lys Ser Glu Asn Gly Val Lys Val Ala Met Gly
                195                 200                 205

Ser Glu Gln Asp Ser Thr Pro Glu Ser Arg His Gly Ala Val Lys Ser
        210                 215                 220

Pro Phe Leu Pro Leu Ala Pro Gln Thr Glu Thr Gln Lys Asn Lys Gln
225                 230                 235                 240

Arg Asn Glu Val Asp Gly Ser Asn Glu Lys Ala Ala Leu Leu Pro Ala
                245                 250                 255

Pro Phe Ser Leu Gly Asp Thr Asn Ile Thr Ile Glu Glu Gln Leu Asn
                260                 265                 270

Ser Ile Asn Leu Ser Phe Gln Asp Asp Pro Asp Ser Ser Thr Ser Thr
        275                 280                 285

Leu Gly Asn Met Leu Glu Leu Pro Gly Thr Ser Ser Ser Thr Ser
        290                 295                 300

Gln Glu Leu Pro Phe
305

<210> SEQ ID NO 4
<211> LENGTH: 2696
<212> TYPE: PRT
<213> ORGANISM: human chromosome

<400> SEQUENCE: 4

Met Asp Gln Thr Cys Glu Leu Pro Arg Arg Asn Cys Leu Leu Pro Phe
1               5                   10                  15

Ser Asn Pro Val Asn Leu Asp Ala Pro Glu Asp Lys Asp Ser Pro Phe
                20                  25                  30

Gly Asn Gly Gln Ser Asn Phe Ser Glu Pro Leu Asn Gly Cys Thr Met
            35                  40                  45

Gln Leu Ser Thr Val Ser Gly Thr Ser Gln Asn Ala Tyr Gly Gln Asp
        50                  55                  60

Ser Pro Ser Cys Tyr Ile Pro Leu Arg Arg Leu Gln Asp Leu Ala Ser
65                  70                  75                  80

Met Ile Asn Val Glu Tyr Leu Asn Gly Ser Ala Asp Gly Ser Glu Ser
                85                  90                  95

Phe Gln Asp Pro Glu Lys Ser Asp Ser Arg Ala Gln Thr Pro Ile Val
                100                 105                 110

Cys Thr Ser Leu Ser Pro Gly Gly Pro Thr Ala Leu Ala Met Lys Gln
            115                 120                 125

Glu Pro Ser Cys Asn Asn Ser Pro Glu Leu Gln Val Lys Val Thr Lys
        130                 135                 140

Thr Ile Lys Asn Gly Phe Leu His Phe Glu Asn Phe Thr Cys Val Asp
145                 150                 155                 160

Asp Ala Asp Val Asp Ser Glu Met Asp Pro Glu Gln Pro Val Thr Glu
                165                 170                 175
```

```
Asp Glu Ser Ile Glu Glu Ile Phe Glu Glu Thr Gln Thr Asn Ala Thr
            180                 185                 190
Cys Asn Tyr Glu Thr Lys Ser Glu Asn Gly Val Lys Val Ala Met Gly
        195                 200                 205
Ser Glu Gln Asp Ser Thr Pro Glu Ser Arg His Gly Ala Val Lys Ser
    210                 215                 220
Pro Phe Leu Pro Leu Ala Pro Gln Thr Glu Thr Gln Lys Asn Lys Gln
225                 230                 235                 240
Arg Asn Glu Val Asp Gly Ser Asn Glu Lys Ala Ala Leu Leu Pro Ala
                245                 250                 255
Pro Phe Ser Leu Gly Asp Thr Asn Ile Thr Ile Glu Glu Gln Leu Asn
            260                 265                 270
Ser Ile Asn Leu Ser Phe Gln Asp Asp Pro Asp Ser Ser Thr Ser Thr
        275                 280                 285
Leu Gly Asn Met Leu Glu Leu Pro Gly Thr Ser Ser Ser Ser Thr Ser
    290                 295                 300
Gln Glu Leu Pro Phe Cys Gln Pro Lys Lys Ser Thr Pro Leu Lys
305                 310                 315                 320
Tyr Glu Val Gly Asp Leu Ile Trp Ala Lys Phe Lys Arg Arg Pro Trp
                325                 330                 335
Trp Pro Cys Arg Ile Cys Ser Asp Pro Leu Ile Asn Thr His Ser Lys
            340                 345                 350
Met Lys Val Ser Asn Arg Arg Pro Tyr Arg Gln Tyr Tyr Val Glu Ala
        355                 360                 365
Phe Gly Asp Pro Ser Glu Arg Ala Trp Val Ala Gly Lys Ala Ile Val
    370                 375                 380
Met Phe Glu Gly Arg His Gln Phe Glu Glu Leu Pro Val Leu Arg Arg
385                 390                 395                 400
Arg Gly Lys Gln Lys Glu Lys Gly Tyr Arg His Lys Val Pro Gln Lys
                405                 410                 415
Ile Leu Ser Lys Trp Glu Ala Ser Val Gly Leu Ala Glu Gln Tyr Asp
            420                 425                 430
Val Pro Lys Gly Ser Lys Asn Arg Lys Cys Ile Pro Gly Ser Ile Lys
        435                 440                 445
Leu Asp Ser Glu Glu Asp Met Pro Phe Glu Asp Cys Thr Asn Asp Pro
    450                 455                 460
Glu Ser Glu His Asp Leu Leu Asn Gly Cys Leu Lys Ser Leu Ala
465                 470                 475                 480
Phe Asp Ser Glu His Ser Ala Asp Glu Lys Glu Lys Pro Cys Ala Lys
                485                 490                 495
Ser Arg Ala Arg Lys Ser Ser Asp Asn Pro Lys Arg Thr Ser Val Lys
            500                 505                 510
Lys Gly His Ile Gln Phe Glu Ala His Lys Asp Glu Arg Arg Gly Lys
        515                 520                 525
Ile Pro Glu Asn Leu Gly Leu Asn Phe Ile Ser Gly Asp Ile Ser Asp
    530                 535                 540
Thr Gln Ala Ser Asn Glu Leu Ser Arg Ile Ala Asn Ser Leu Thr Gly
545                 550                 555                 560
Ser Asn Thr Ala Pro Gly Ser Phe Leu Phe Ser Ser Cys Gly Lys Asn
                565                 570                 575
Thr Ala Lys Lys Glu Phe Glu Thr Ser Asn Gly Asp Ser Leu Leu Gly
            580                 585                 590
Leu Pro Glu Gly Ala Leu Ile Ser Lys Cys Ser Arg Glu Lys Asn Lys
```

-continued

```
               595                 600                 605
Pro Gln Arg Ser Leu Val Cys Gly Ser Lys Val Lys Leu Cys Tyr Ile
        610                 615                 620
Gly Ala Gly Asp Glu Glu Lys Arg Ser Asp Ser Ile Ser Ile Cys Thr
625                 630                 635                 640
Thr Ser Asp Asp Gly Ser Ser Asp Leu Asp Pro Ile Glu His Ser Ser
                645                 650                 655
Glu Ser Asp Asn Ser Val Leu Glu Ile Pro Asp Ala Phe Asp Arg Thr
            660                 665                 670
Glu Asn Met Leu Ser Met Gln Lys Asn Glu Lys Ile Lys Tyr Ser Arg
        675                 680                 685
Phe Ala Ala Thr Asn Thr Arg Val Lys Ala Lys Gln Lys Pro Leu Ile
    690                 695                 700
Ser Asn Ser His Thr Asp His Leu Met Gly Cys Thr Lys Ser Ala Glu
705                 710                 715                 720
Pro Gly Thr Glu Thr Ser Gln Val Asn Leu Ser Asp Leu Lys Ala Ser
                725                 730                 735
Thr Leu Val His Lys Pro Gln Ser Asp Phe Thr Asn Asp Ala Leu Ser
            740                 745                 750
Pro Lys Phe Asn Leu Ser Ser Ser Ile Ser Ser Glu Asn Ser Leu Ile
        755                 760                 765
Lys Gly Gly Ala Ala Asn Gln Ala Leu Leu His Ser Lys Ser Lys Gln
    770                 775                 780
Pro Lys Phe Arg Ser Ile Lys Cys Lys His Lys Glu Asn Pro Val Met
785                 790                 795                 800
Ala Glu Pro Pro Val Ile Asn Glu Glu Cys Ser Leu Lys Cys Cys Ser
                805                 810                 815
Ser Asp Thr Lys Gly Ser Pro Leu Ala Ser Ile Ser Lys Ser Gly Lys
            820                 825                 830
Val Asp Gly Leu Lys Leu Leu Asn Asn Met His Glu Lys Thr Arg Asp
        835                 840                 845
Ser Ser Asp Ile Glu Thr Ala Val Val Lys His Val Leu Ser Glu Leu
    850                 855                 860
Lys Glu Leu Ser Tyr Arg Ser Leu Gly Glu Asp Val Ser Asp Ser Gly
865                 870                 875                 880
Thr Ser Lys Pro Ser Lys Pro Leu Leu Phe Ser Ser Ala Ser Ser Gln
                885                 890                 895
Asn His Ile Pro Ile Glu Pro Asp Tyr Lys Phe Ser Thr Leu Leu Met
            900                 905                 910
Met Leu Lys Asp Met His Asp Ser Lys Thr Lys Glu Gln Arg Leu Met
        915                 920                 925
Thr Ala Gln Asn Leu Val Ser Tyr Arg Ser Pro Gly Arg Gly Asp Cys
    930                 935                 940
Ser Thr Asn Ser Pro Val Gly Val Ser Lys Val Leu Val Ser Gly Gly
945                 950                 955                 960
Ser Thr His Asn Ser Glu Lys Lys Gly Asp Gly Thr Gln Asn Ser Ala
                965                 970                 975
Asn Pro Ser Pro Ser Gly Gly Asp Ser Ala Leu Ser Gly Glu Leu Ser
            980                 985                 990
Ala Ser Leu Pro Gly Leu Leu Ser  Asp Lys Arg Asp Leu  Pro Ala Ser
        995                1000                  1005
Gly Lys  Ser Arg Ser Asp Cys  Val Thr Arg Arg Asn  Cys Gly Arg
      1010                1015                  1020
```

```
Ser Lys Pro Ser Ser Lys Leu Arg Asp Ala Phe Ser Ala Gln Met
    1025                1030                1035

Val Lys Asn Thr Val Asn Arg Lys Ala Leu Lys Thr Glu Arg Lys
    1040                1045                1050

Arg Lys Leu Asn Gln Leu Pro Ser Val Thr Leu Asp Ala Val Leu
    1055                1060                1065

Gln Gly Asp Arg Glu Arg Gly Gly Ser Leu Arg Gly Gly Ala Glu
    1070                1075                1080

Asp Pro Ser Lys Glu Asp Pro Leu Gln Ile Met Gly His Leu Thr
    1085                1090                1095

Ser Glu Asp Gly Asp His Phe Ser Asp Val His Phe Asp Ser Lys
    1100                1105                1110

Val Lys Gln Ser Asp Pro Gly Lys Ile Ser Glu Lys Gly Leu Ser
    1115                1120                1125

Phe Glu Asn Gly Lys Gly Pro Glu Leu Asp Ser Val Met Asn Ser
    1130                1135                1140

Glu Asn Asp Glu Leu Asn Gly Val Asn Gln Val Val Pro Lys Lys
    1145                1150                1155

Arg Trp Gln Arg Leu Asn Gln Arg Arg Thr Lys Pro Arg Lys Arg
    1160                1165                1170

Met Asn Arg Phe Lys Glu Lys Glu Asn Ser Glu Cys Ala Phe Arg
    1175                1180                1185

Val Leu Leu Pro Ser Asp Pro Val Gln Glu Gly Arg Asp Glu Phe
    1190                1195                1200

Pro Glu His Arg Thr Pro Ser Ala Ser Ile Leu Glu Glu Pro Leu
    1205                1210                1215

Thr Glu Gln Asn His Ala Asp Cys Leu Asp Ser Ala Gly Pro Arg
    1220                1225                1230

Leu Asn Val Cys Asp Lys Ser Ser Ala Ser Ile Gly Asp Met Glu
    1235                1240                1245

Lys Glu Pro Gly Ile Pro Ser Leu Thr Pro Gln Ala Glu Leu Pro
    1250                1255                1260

Glu Pro Ala Val Arg Ser Glu Lys Lys Arg Leu Arg Lys Pro Ser
    1265                1270                1275

Lys Trp Leu Leu Glu Tyr Thr Glu Glu Tyr Asp Gln Ile Phe Ala
    1280                1285                1290

Pro Lys Lys Gln Lys Lys Val Gln Glu Gln Val His Lys Val
    1295                1300                1305

Ser Ser Arg Cys Glu Glu Glu Ser Leu Leu Ala Arg Gly Arg Ser
    1310                1315                1320

Ser Ala Gln Asn Lys Gln Val Asp Glu Asn Ser Leu Ile Ser Thr
    1325                1330                1335

Lys Glu Glu Pro Pro Val Leu Glu Arg Glu Ala Pro Phe Leu Glu
    1340                1345                1350

Gly Pro Leu Ala Gln Ser Glu Leu Gly Gly Gly His Ala Glu Leu
    1355                1360                1365

Pro Gln Leu Thr Leu Ser Val Pro Val Ala Pro Glu Val Ser Pro
    1370                1375                1380

Arg Pro Ala Leu Glu Ser Glu Glu Leu Leu Val Lys Thr Pro Gly
    1385                1390                1395

Asn Tyr Glu Ser Lys Arg Gln Arg Lys Pro Thr Lys Lys Leu Leu
    1400                1405                1410
```

-continued

| | | | | | | | | | | | |
|---|---|---|---|---|---|---|---|---|---|---|---|
| Glu | Ser 1415 | Asn | Asp | Leu 1420 | Asp | Pro | Gly | Phe | Met 1425 | Pro | Lys | Lys | Gly | Asp |
| Leu | Gly 1430 | Leu | Ser | Lys 1435 | Lys | Cys | Tyr | Glu | Ala 1440 | Gly | His | Leu | Glu | Asn |
| Gly | Ile 1445 | Thr | Glu | Ser 1450 | Cys | Ala | Thr | Ser | Tyr 1455 | Ser | Lys | Asp | Phe | Gly |
| Gly | Gly 1460 | Thr | Thr | Lys 1465 | Ile | Phe | Asp | Lys | Pro 1470 | Arg | Lys | Arg | Lys | Arg |
| Gln | Arg 1475 | His | Ala | Ala 1480 | Ala | Lys | Met | Gln | Cys 1485 | Lys | Lys | Val | Lys | Asn |
| Asp | Asp 1490 | Ser | Ser | Lys 1495 | Glu | Ile | Pro | Gly | Ser 1500 | Glu | Gly | Glu | Leu | Met |
| Pro | His 1505 | Arg | Thr | Ala 1510 | Thr | Ser | Pro | Lys | Glu 1515 | Thr | Val | Glu | Glu | Gly |
| Val | Glu 1520 | His | Asp | Pro 1525 | Gly | Met | Pro | Ala | Ser 1530 | Lys | Lys | Met | Gln | Gly |
| Glu | Arg 1535 | Gly | Gly | Gly 1540 | Ala | Ala | Leu | Lys | Glu 1545 | Asn | Val | Cys | Gln | Asn |
| Cys | Glu 1550 | Lys | Leu | Gly 1555 | Glu | Leu | Leu | Cys | Glu 1560 | Ala | Gln | Cys | Cys |
| Gly | Ala 1565 | Phe | His | Leu 1570 | Glu | Cys | Leu | Gly | Leu 1575 | Thr | Glu | Met | Pro | Arg |
| Gly | Lys 1580 | Phe | Ile | Cys 1585 | Asn | Glu | Cys | Arg | Thr 1590 | Gly | Ile | His | Thr | Cys |
| Phe | Val 1595 | Cys | Lys | Gln 1600 | Ser | Gly | Glu | Asp | Val 1605 | Lys | Arg | Cys | Leu | Leu |
| Pro | Leu 1610 | Cys | Gly | Lys 1615 | Phe | Tyr | His | Glu | Glu 1620 | Cys | Val | Gln | Lys | Tyr |
| Pro | Pro 1625 | Thr | Val | Met 1630 | Gln | Asn | Lys | Gly | Phe 1635 | Arg | Cys | Ser | Leu | His |
| Ile | Cys 1640 | Ile | Thr | Cys 1645 | His | Ala | Ala | Asn | Pro 1650 | Ala | Asn | Val | Ser | Ala |
| Ser | Lys 1655 | Gly | Arg | Leu 1660 | Met | Arg | Cys | Val | Arg 1665 | Cys | Pro | Val | Ala | Tyr |
| His | Ala 1670 | Asn | Asp | Phe 1675 | Cys | Leu | Ala | Ala | Gly 1680 | Ser | Lys | Ile | Leu | Ala |
| Ser | Asn 1685 | Ser | Ile | Ile 1690 | Cys | Pro | Asn | His | Phe 1695 | Thr | Pro | Arg | Arg | Gly |
| Cys | Arg 1700 | Asn | His | Glu 1705 | His | Val | Asn | Val | Ser 1710 | Trp | Cys | Phe | Val | Cys |
| Ser | Glu 1715 | Gly | Gly | Ser 1720 | Leu | Leu | Cys | Cys | Asp 1725 | Ser | Cys | Pro | Ala | Ala |
| Phe | His 1730 | Arg | Glu | Cys 1735 | Leu | Asn | Ile | Asp | Ile 1740 | Pro | Glu | Gly | Asn | Trp |
| Tyr | Cys 1745 | Asn | Asp | Cys 1750 | Lys | Ala | Gly | Lys | Lys 1755 | Pro | His | Tyr | Arg | Glu |
| Ile | Val 1760 | Trp | Val | Lys 1765 | Val | Gly | Arg | Tyr | Arg 1770 | Trp | Trp | Pro | Ala | Glu |
| Ile | Cys 1775 | His | Pro | Arg 1780 | Ala | Val | Pro | Ser | Asn 1785 | Ile | Asp | Lys | Met | Arg |
| His | Asp 1790 | Val | Gly | Glu 1795 | Phe | Pro | Val | Leu | Phe 1800 | Phe | Gly | Ser | Asn | Asp |
| Tyr | Leu | Trp | Thr | His | Gln | Ala | Arg | Val | Phe | Pro | Tyr | Met | Glu | Gly |

-continued

```
            1805                1810                1815

Asp Val Ser Ser Lys Asp Lys Met Gly Lys Gly Val Asp Gly Thr
    1820                1825                1830

Tyr Lys Lys Ala Leu Gln Glu Ala Ala Ala Arg Phe Glu Glu Leu
    1835                1840                1845

Lys Ala Gln Lys Glu Leu Arg Gln Leu Gln Glu Asp Arg Lys Asn
    1850                1855                1860

Asp Lys Lys Pro Pro Pro Tyr Lys His Ile Lys Val Asn Arg Pro
    1865                1870                1875

Ile Gly Arg Val Gln Ile Phe Thr Ala Asp Leu Ser Glu Ile Pro
    1880                1885                1890

Arg Cys Asn Cys Lys Ala Thr Asp Glu Asn Pro Cys Gly Ile Asp
    1895                1900                1905

Ser Glu Cys Ile Asn Arg Met Leu Leu Tyr Glu Cys His Pro Thr
    1910                1915                1920

Val Cys Pro Ala Gly Gly Arg Cys Gln Asn Gln Cys Phe Ser Lys
    1925                1930                1935

Arg Gln Tyr Pro Glu Val Glu Ile Phe Arg Thr Leu Gln Arg Gly
    1940                1945                1950

Trp Gly Leu Arg Thr Lys Thr Asp Ile Lys Lys Gly Glu Phe Val
    1955                1960                1965

Asn Glu Tyr Val Gly Glu Leu Ile Asp Glu Glu Glu Cys Arg Ala
    1970                1975                1980

Arg Ile Arg Tyr Ala Gln Glu His Asp Ile Thr Asn Phe Tyr Met
    1985                1990                1995

Leu Thr Leu Asp Lys Asp Arg Ile Ile Asp Ala Gly Pro Lys Gly
    2000                2005                2010

Asn Tyr Ala Arg Phe Met Asn His Cys Cys Gln Pro Asn Cys Glu
    2015                2020                2025

Thr Gln Lys Trp Ser Val Asn Gly Asp Thr Arg Val Gly Leu Phe
    2030                2035                2040

Ala Leu Ser Asp Ile Lys Ala Gly Thr Glu Leu Thr Phe Asn Tyr
    2045                2050                2055

Asn Leu Glu Cys Leu Gly Asn Gly Lys Thr Val Cys Lys Cys Gly
    2060                2065                2070

Ala Pro Asn Cys Ser Gly Phe Leu Gly Val Arg Pro Lys Asn Gln
    2075                2080                2085

Pro Ile Ala Thr Glu Glu Lys Ser Lys Lys Phe Lys Lys Lys Gln
    2090                2095                2100

Gln Gly Lys Arg Arg Thr Gln Gly Glu Ile Thr Lys Glu Arg Glu
    2105                2110                2115

Asp Glu Cys Phe Ser Cys Gly Asp Ala Gly Gln Leu Val Ser Cys
    2120                2125                2130

Lys Lys Pro Gly Cys Pro Lys Val Tyr His Ala Asp Cys Leu Asn
    2135                2140                2145

Leu Thr Lys Arg Pro Ala Gly Lys Trp Glu Cys Pro Trp His Gln
    2150                2155                2160

Cys Asp Ile Cys Gly Lys Glu Ala Ala Ser Phe Cys Glu Met Cys
    2165                2170                2175

Pro Ser Ser Phe Cys Lys Gln His Arg Glu Gly Met Leu Phe Ile
    2180                2185                2190

Ser Lys Leu Asp Gly Arg Leu Ser Cys Thr Glu His Asp Pro Cys
    2195                2200                2205
```

-continued

```
Gly Pro Asn Pro Leu Glu Pro Gly Glu Ile Arg Glu Tyr Val Pro
    2210            2215                2220

Pro Pro Val Pro Leu Pro Pro Gly Pro Ser Thr His Leu Ala Glu
    2225            2230                2235

Gln Ser Thr Gly Met Ala Ala Gln Ala Pro Lys Met Ser Asp Lys
    2240            2245                2250

Pro Pro Ala Asp Thr Asn Gln Met Leu Ser Leu Ser Lys Lys Ala
    2255            2260                2265

Leu Ala Gly Thr Cys Gln Arg Pro Leu Leu Pro Glu Arg Pro Leu
    2270            2275                2280

Glu Arg Thr Asp Ser Arg Pro Gln Pro Leu Asp Lys Val Arg Asp
    2285            2290                2295

Leu Ala Gly Ser Gly Thr Lys Ser Gln Ser Leu Val Ser Ser Gln
    2300            2305                2310

Arg Pro Leu Asp Arg Pro Pro Ala Val Ala Gly Pro Arg Pro Gln
    2315            2320                2325

Leu Ser Asp Lys Pro Ser Pro Val Thr Ser Pro Ser Ser Ser Pro
    2330            2335                2340

Ser Val Arg Ser Gln Pro Leu Glu Arg Pro Leu Gly Thr Ala Asp
    2345            2350                2355

Pro Arg Leu Asp Lys Ser Ile Gly Ala Ala Ser Pro Arg Pro Gln
    2360            2365                2370

Ser Leu Glu Lys Thr Ser Val Pro Thr Gly Leu Arg Leu Pro Pro
    2375            2380                2385

Pro Asp Arg Leu Leu Ile Thr Ser Ser Pro Lys Pro Gln Thr Ser
    2390            2395                2400

Asp Arg Pro Thr Asp Lys Pro His Ala Ser Leu Ser Gln Arg Leu
    2405            2410                2415

Pro Pro Pro Glu Lys Val Leu Ser Ala Val Val Gln Thr Leu Val
    2420            2425                2430

Ala Lys Glu Lys Ala Leu Arg Pro Val Asp Gln Asn Thr Gln Ser
    2435            2440                2445

Lys Asn Arg Ala Ala Leu Val Met Asp Leu Ile Asp Leu Thr Pro
    2450            2455                2460

Arg Gln Lys Glu Arg Ala Ala Ser Pro His Gln Val Thr Pro Gln
    2465            2470                2475

Ala Asp Glu Lys Met Pro Val Leu Glu Ser Ser Ser Trp Pro Ala
    2480            2485                2490

Ser Lys Gly Leu Gly His Met Pro Arg Ala Val Glu Lys Gly Cys
    2495            2500                2505

Val Ser Asp Pro Leu Gln Thr Ser Gly Lys Ala Ala Ala Pro Ser
    2510            2515                2520

Glu Asp Pro Trp Gln Ala Val Lys Ser Leu Thr Gln Ala Arg Leu
    2525            2530                2535

Leu Ser Gln Pro Pro Ala Lys Ala Phe Leu Tyr Glu Pro Thr Thr
    2540            2545                2550

Gln Ala Ser Gly Arg Ala Ser Ala Gly Ala Glu Gln Thr Pro Gly
    2555            2560                2565

Pro Leu Ser Gln Ser Pro Gly Leu Val Lys Gln Ala Lys Gln Met
    2570            2575                2580

Val Gly Gly Gln Gln Leu Pro Ala Leu Ala Ala Lys Ser Gly Gln
    2585            2590                2595
```

```
Ser Phe Arg Ser Leu Gly Lys Ala Pro Ala Ser Leu Pro Thr Glu
    2600            2605                2610

Glu Lys Lys Leu Val Thr Thr Glu Gln Ser Pro Trp Ala Leu Gly
    2615            2620                2625

Lys Ala Ser Ser Arg Ala Gly Leu Trp Pro Ile Val Ala Gly Gln
    2630            2635                2640

Thr Leu Ala Gln Ser Cys Trp Ser Ala Gly Ser Thr Gln Thr Leu
    2645            2650                2655

Ala Gln Thr Cys Trp Ser Leu Gly Arg Gly Gln Asp Pro Lys Pro
    2660            2665                2670

Glu Gln Asn Thr Leu Pro Ala Leu Asn Gln Ala Pro Ser Ser His
    2675            2680                2685

Lys Cys Ala Glu Ser Glu Gln Lys
    2690            2695
```

<210> SEQ ID NO 5
<211> LENGTH: 190
<212> TYPE: DNA
<213> ORGANISM: human chromosome

<400> SEQUENCE: 5

```
gtcacattag ctaggacttc cagtacaatg ctgaaaagga gtagtgagga gacatccttg      60
ccttatccct gatcttagta ggaatgcttc aagttttttca ccattaggta tgatattagt   120
ggcaggtttt ttgtagatgt tctttctgaa gttgaggaag ttcccctcta ttcctagttt   180
gctggaaggc                                                           190
```

<210> SEQ ID NO 6
<211> LENGTH: 275
<212> TYPE: DNA
<213> ORGANISM: human chromosome

<400> SEQUENCE: 6

```
acttttgaa agtttcattt aggtgctatc atttaaaaaa tcagaagata tcacttaaga       60
atccagcatt ctagtttctt tcgaaaaatc agaagatctg caacactag cccacattc     120
cggcatggca acaaccagct agagcggtgc tggctgttcc ccctctgtgg ggcttgtgct   180
ctggtttctg aagtcctaac cctcaccagg cccaactgcc acctacgcca gctgcatggc   240
ccctacactg tgtctctgca cgaggcagcc ccaat                              275
```

<210> SEQ ID NO 7
<211> LENGTH: 20
<212> TYPE: DNA
<213> ORGANISM: artificial sequence
<220> FEATURE:
<223> OTHER INFORMATION: This sequence is a primer for amplifying cDNAs
      in a PCR analysis.

<400> SEQUENCE: 7

```
atttgtgaat gagtatgtgg                                                 20
```

<210> SEQ ID NO 8
<211> LENGTH: 20
<212> TYPE: DNA

-continued

```
<213> ORGANISM: Artificial sequence
<220> FEATURE:
<223> OTHER INFORMATION: This sequence is a primer for amplifying cDNAs
      in a PCR analysis.

<400> SEQUENCE: 8
ctaaaacact catcttctcg                                                   20
```

NUCLEIC ACID, PROBE COMPRISING THE NUCLEIC ACID AND SCREENING METHOD USING THE PROBE

BACKGROUND OF THE INVENTION

1. Field of the Invention

This invention relates to a nucleic acid, a probe and a screening method using such a probe, and more particularly to a nucleic acid, a probe comprising the nucleic acid and a screening method using the probe for a gene diagnosis.

2. Description of Related Art

As a gene mapping method of positioning a human genome on a chromosome to make a chromosomal map, there have been popularly practiced a method wherein a remaining specific human chromosome or a part of the chromosome is analyzed by using a clone panel of a somatic cell hybrid or a partially deletion chromosome between a human and a rodent, and a method wherein a cloned gene is used as a probe in a Southern blotting.

Lately, there is used a so-called in situ hybridization wherein a gene or DNA marker cloned and labeled from genome DNA is used as a probe and a molecule hybrid is directly formed in a chromosome sample on a slide glass to detect a gene existing part in order to efficiently obtain information on specified sites of many genes such as human genes and a mutual sequence order.

As the in situ hybridization, there are a method wherein DNA labeled with a radioisotope (mainly $^3$H) is used as a probe and its site is detected by an autoradiography, and a method wherein a fluorescence signal of a labeled DNA probe is detected by means of a fluorescence microscope.

The latter fluorescence in situ hybridization method (hereinafter referred to as FISH method) is excellent in points that an RI equipment is useless, and an operating procedure is simple, and a minute mapping is exactly carried out on a chromosome band for a short time (2 days).

At present, probes useful for various diseases/syndromes are developed for using these methods to make a clinic diagnosis. For example, there is known to be an inspection probe suitable for the FISH method on various chromosomes aimed at a syndrome having a microdeletion of a congenital anomaly syndrome. Such a probe inspects a gene of a target disease, and if an inspection result is positive (i.e. a deletion or the like is existent), the confirmed diagnosis is made.

For example, the above probe is effective for a Prader Willi syndrome because about 60% of patients have a deletion.

As mentioned above, useful probes have been found in a part of cloning of genes for the diseases. However, there are still idiopathic diseases, and inspection and diagnosis methods effective thereto are not found except for physical findings and symptoms of the disease. If a probe can be found by using a gene and/or a homolog resulted in these diseases, it becomes very beneficial in the filed of a gene diagnosis.

SUMMARY OF THE INVENTION

It is, therefore, an object of the invention to provide a nucleic acid, a useful probe using the nucleic acid and a screening method using such a probe.

In order to achieve the above object, the inventors have made various studies with respect to a relationship between a congenital anomaly syndrome and a gene and found out a probe and a screening method using such a probe according to the invention.

The nucleic acid according to a first aspect of the invention is (a) a nucleic acid comprising a base sequence shown in base numbers 1–39726 of SEQ ID NO: 1, or (b) a nucleic acid wherein a part of the bases 1–39726 of SEQ ID NO: 1 is deleted, substituted or added, and the nucleic acid has a homology of 80% for the base sequence.

Furthermore, the nucleic acid according to a second aspect of the invention is (a) a nucleic acid comprising a base sequence shown in base numbers 1–8511 of SEQ ID NO: 2, or (b) a nucleic acid wherein a part of the bases 1–8511 of SEQ ID NO: 2 is deleted, substituted or added, and the nucleic acid has a homology of 80% for the base sequence.

The probe according to a third aspect of the invention comprises the nucleic acid as defined in the first or second aspect of the invention.

In a preferable embodiment, the probe according to the invention is used as a diagnosis for Sotos syndrome.

The peptide fragment according to a fourth aspect of the invention is (a) a peptide fragment comprising an amino acid sequence shown in amino acid numbers 1–309 of SEQ ID NO: 3, or (b) a peptide fragment wherein a part of the amino acid sequence shown in SEQ ID NO: 3 is deleted, substituted or added, and the peptide fragment has a homology of 80% for the base sequence.

The peptide fragment according to a fifth aspect of the invention is (a) a peptide fragment comprising an amino acid sequence shown in amino acid numbers 1–2696 of SEQ ID NO: 4, or (b) a peptide fragment wherein a part of the amino acid sequence shown in SEQ ID NO: 4 is deleted, substituted or added, and the peptide fragment has a homology of 80% for the base sequence.

The probe according to a sixth aspect of the invention comprises the peptide fragment as defined in the fourth or fifth aspect of the invention.

A probe for using as a diagnosis for Sotos syndrome according to the invention, is characterized in that the probe comprises the following (a) or (b) on the human chromosome 5:
  (a) a nucleic acid comprising a base sequence shown in base numbers 1–190 of SEQ ID NO: 5, or
  (b) a nucleic acid wherein a part of the bases 1–190 of SEQ ID NO: 5 is deleted, substituted or added, and having a homology of 80% for the base sequence.

A probe for using as a diagnosis for Sotos syndrome according to the invention, is characterized in that the probe comprises the following (a) or (b) on the human chromosome 5:
  (a) a nucleic acid comprising a base sequence shown in base numbers 1–275 of SEQ ID NO: 6,or
  (b) a nucleic acid wherein a part of the bases 1–275 of SEQ ID NO: 6 is deleted, substituted or added, and having a homology of 80% for the base sequence.

A probe for using as a diagnosis for Sotos syndrome according to the invention, is characterized in that the probe comprises any sequence existed in between the following (a) and (b) on the human chromosome 5:
  (a) a nucleic acid comprising a base sequence shown in base numbers 1–190 of SEQ ID NO: 5, and
  (b) a nucleic acid comprising a base sequence shown in bases 1–275 of SEQ ID NO: 6.

The screening method according to a seventh aspect of the invention is characterized by using the probe as defined in the third, forth or seventh to tenth aspect of the invention.

In a preferable embodiment of the screening method according to the invention, the screening is carried out by using at least one selected from the group consisting of an in situ hybridization method, a Southern blotting method, a macroarray-based hybridization method and a base sequence determination method (Dideoxy chain termination method and the like).

In a preferable embodiment of the screening method according to the invention, the in situ hybridization method is a fluorescence in situ hybridization method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be described with reference to the accompanying drawings, wherein.

DETAILED DESCRIPTION OF THE INVENTION

Figure 1:
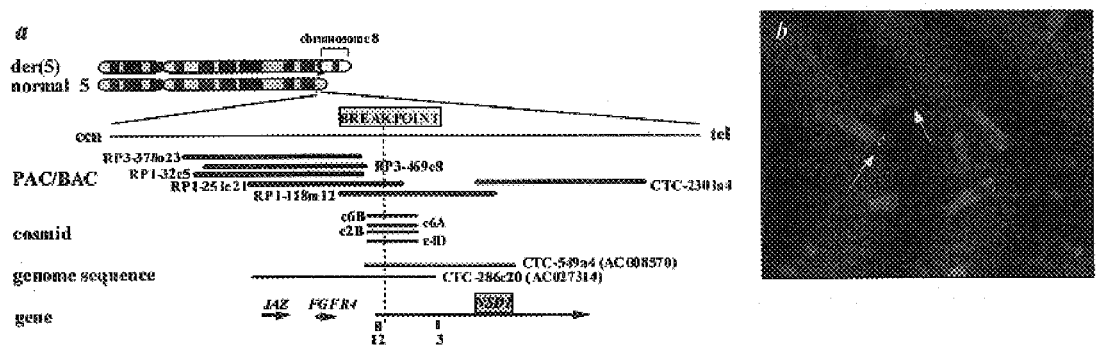
FIG. 1 is a view showing a physical mapping.

First of all, the nucleic acid according to the invention is explained. The nucleic acid according to the invention is (a) a nucleic acid comprising a base sequence shown in base numbers 1–39726 of SEQ ID NO: 1, or (b) a nucleic acid wherein a part of base numbers 1–39726 of SEQ ID NO: 1 is deleted, substituted or added, and the nucleic acid has a homology of 80%, preferably 90%, more preferably 95% for the base sequence. Such a nucleic acid is derived from NSD1 of a human chromosome 5 and is complementary with a part of the NSD1. Concretely, it is a nucleic acid complementary with a genomic DNA including an exon 1, an exon 2 and an intron of the NSD1. Also, the nucleic acid according to the invention includes a nucleic acid wherein a part of base numbers 1–39726 of SEQ ID NO: 1 is deleted, substituted or added, and the nucleic acid has a homology of 80%, preferably 90%, more preferably 95% for the base sequence. Even if the part is deleted, substituted or added, the latter nucleic acid can be utilized as a probe as mentioned later.

Further, the nucleic acid according to the invention comprises a base sequence shown in base numbers 1–8511 of SEQ ID NO: 2. Such a nucleic acid is derived from NSD1 of a human chromosome 5, and is complementary with a part of the NSD1. Concretely, this is a nucleic acid complementary with a cDNA including exons 1–23 of the NSD1. Also, the nucleic acid according to the invention includes a nucleic acid wherein a part of the base numbers 1–8511 of SEQ ID NO: 2 is deleted, substituted or added, and the nucleic acid has a homology of 80%, preferably 90%, more preferably 95% for the base sequence.

In addition, an amino acid sequence corresponding to a base sequence shown in SEQ ID NO: 2 is as follows. Such an amino acid sequence is shown in SEQ ID NO: 4. A translation region of the base sequence in SEQ ID NO: 1, i.e. an amino acid sequence corresponding to the second exon of the NSD1 is shown in SEQ ID NO: 3.

The peptide fragment according to the invention is (a) a peptide fragment comprising an amino acid sequence shown in amino acid numbers 1–309 of SEQ ID NO: 3, or (b) a peptide fragment wherein a part of the amino acids in SEQ ID NO: 3 is deleted, substituted or added, and the amino acid sequence has a homology of 80%, preferably 90%, more preferably 95% for the amino acid sequence. Also, the peptide fragment according to the invention is (a) a peptide fragment comprising an amino acid sequence shown in amino acid numbers 1–2696 of SEQ ID NO: 4, or (b) a peptide fragment wherein a part of the amino acids in SEQ ID NO: 4 is deleted, substituted or added, and the amino acid sequence has a homology of 80%, preferably 90%, more preferably 95% for the amino acid sequence. Such amino acid sequences can be used for an immunologic test utilizing an antigen antibody reaction.

With respect to the aforementioned nucleic acids, a purification and isolation method will be described below. The above nucleic acid, not particularly limited, can be purified and isolated by the following procedure. This nucleic acid includes exons 1 and 2 of NSD1 and is obtained by subcloning a PAC clone called a RP1-118m12 according to the following method. At first, a PAC DNA is purified. Then, the purified PAC DNA is isolated by using a Midi-Prep column (Qiagen, Chatsworth, Calif.) and partially digested by using a restriction enzyme such as Sau3AI. Next, a SuperCos1 cosmid vector is prepared according to manufacturer's instructions (Stratagene, La Jolla, Calif.) and ligated to the digested PAC DNA using T4DNA ligase. The ligation reaction products are packaged using the Gigapack III gold extract (Stratagene) and transfected into XL1-Blue MR host cells. A genomic sequence is constructed by means of STS content mapping using a PCR. Thus, a nucleic acid according to the invention can be obtained.

Moreover, a base sequence of DNA can be determined by any method well known in those skilled in the art. For example, the base sequence can be determined by using a terminator method or the like.

As a method of using the probe according to the invention, the above nucleic acid is amplified directly or by a PCR method and immobilized by blotting on a polymer membrane and then subjected to a hybridization. The hybridization is not particularly limited according to usual manner, but may include, for example, a Southern blotting method, an in situ hybridization method, a microarray-based method and a base sequence determination method. The in situ hybridization method is preferable from a viewpoint of a quick and accurate screening. As the in situ hybridization method, there are a fluorescence in situ hybridization method (hereinafter referred to as FISH method), a radioisotope in situ hybridization method and the like. The FISH method is preferable from a viewpoint that an RI equipment is not required. In the FISH method, it is general that a chromosome sample is prepared on a slide glass, hybridized with a labelled probe, and directly investigated by a microscope.

As a support medium used in the hybridization of the probe according to the invention, mention may be made of a thin film, a powder, a particulate matter, a gel, a bead, a fiber, a glass, a dispersion liquid, an emulsion and so on. They may be used by filling into an adequate column. Among them, the thin film such as a nitrocellulose film or a nylon film is preferable.

An example of the label used in the probe according to the invention is explained. As the label, use may be made of ones well known by persons skilled in the art. The label is not particularly limited, but includes, for example, a radioactive atom such as $^{32}P$, $^{35}S$ or the like, a biotin group, an avidin group, an enzyme, a fluorescence label and so on. In the case of utilizing an antigen-antibody system, the label may contain an antigen, which is included within the scope of the invention.

The nucleic acid according to the invention complementarily bonds with a part of a normal chromosome 5. However, if the chromosome 5 has an abnormality, that is, a deletion abnormality, the nucleic acid according to the invention does not bond with such an abnormal chromosome 5. When the nucleic acid according to the invention is used as a probe by utilizing the above property, the abnormality of the chromosome 5 can be confirmed. Therefore, the prove according to the invention can also be used as a diagnostic probe for a Sotos syndrome having a deletion of the chromosome 5 in 60% of patients with Sotos syndrome.

A probe for using as a diagnosis for Sotos syndrome according to the invention, comprises the following (a) or (b) on the human chromosome 5:

(a) a nucleic acid comprising a base sequence shown in base numbers 1–190 of SEQ ID NO: 5, or (b) a nucleic acid wherein a part of the bases 1–190 of SEQ ID NO: 5 is deleted, substituted or added, and having a homology of 80% for the base sequence.

A probe for using as a diagnosis for Sotos syndrome according to the invention, comprises the following (a) or (b) on the human chromosome 5:

(a) a nucleic acid comprising a base sequence shown in base numbers 1–275 of SEQ ID NO: 6, or (b) a nucleic acid wherein a part of the bases 1–275 of SEQ ID NO: 6 is deleted, substituted or added, and having a homology of 80% for the base sequence.

A probe for using as a diagnosis for Sotos syndrome according to the invention, comprises any sequence existing between the following (a) and (b) on the human chromosome 5:

(a) a nucleic acid comprising a base sequence shown in base numbers 1–190 of SEQ ID NO: 5, and (b) a nucleic acid comprising a base sequence shown in base numbers 1–275 of SEQ ID NO: 6.

These probes can be used for this is dependent on a finding from the inventors in that the case sequence is deleted, which existed in between a sequence as in SEQ ID NO: 5 and a sequence as in SEQ ID NO: 6 on the chromosome 5 of a patient suffered from Sotos syndrome. Therefore, the base sequence of SEQ ID NO: 5 may be used by itself as a probe, the base sequence of SEQ ID NO: 6 may be used by itself as a probe. Also, since a sequence existed in a normal human at between the above SEQ ID NO: 5 and SEQ ID NO: 6 does not exist in a patient suffering from Sotos syndrome, any sequences of them may be used for a diagnosis of Sotos syndrome. A base length of the probe, depending on the method of screening, is not particularly limited, but 5 kb or more than 5 kb. Particularly, 5–15 kb is preferable, 7–12 kb is more preferable.

Although the sequence of the above SEQ ID NO: 5 and SEQ ID NO: 6 exists in the normal human, since 1 copy of the chromosome of a patient suffered from Sotos syndrome is deleted, a gene diagnosis may be carried out by these fact.

The following examples are given in illustration of the invention and are not intended as limitations thereof.

The following examples are intended to illustrate an embodiment of the invention, and it is naturally possible to properly change the invention without departing from the spirit and the scope of the invention claimed in claims.

EXAMPLE 1

Sotos syndrome (SS, OMIM 117550), also known as cerebral gigantism, is a neurological disorder characterized by prenatal-childhood overgrowth with advanced bone age, a peculiar face with large skull, acromegalic features and pointed chin, occasional brain anomalies and seizures, and mental retardation.

Although most cases are sporadic, occasional parent-child transmissions of the disease are known. SS patients are estimated to have a 3.9% risk of benign/malignant tumors. Firstly, NSD1 gene is isolated by positional cloning from the 5q35 breakpoint of a patient with a de novo t(5;8)(q35;q24.1). The gene encodes 2,696 amino acids with SET, PHD finger and PWWP domains, and interacts with nuclear receptors (NRs). Among 38 SS patients examined by direct sequencing, four de novo point mutations including a nonsense mutation (1310C->A, S437X), a one-bp deletion (3536delA), a one-bp insertion (5998insT) and a splice-donor-site mutation (6135+1G->A) are detected in NSD1 (10.5%). Also, 20 submicroscopic deletions (66.7%) involving NSD1 are identified in 30 SS patients whose metaphase and/or interphase cells are available for FISH studies. Overall, 77% of SS patients are estimated to have NSD1 mutations. These results indicate that haploinsufficiency of NSD1 causes Sotos syndrome and NSD1 plays a significant role in growth and brain development in human.

There is adopted a girl with Sotos syndrome (SS) associated with de novo reciprocal translocation, 46, XX, t(5;8)(q35;q24.1) (patient BP). A 5q35 region is likely to harbor a gene locus for SS, because there are another translocation [t(5;15)(q35;q24.1)] and a deletion involving 5q35[del(5)(q35.1qter)] associated with SS or SS-like features, respectively. Therefore, the 5q35 breakpoint is cloned. At first, FGFR4 is focused, as it is mapped to 5q35-qter and mutations in its gene family are known to be associated with some craniofacial and growth abnormalities. Then, a PAC clone (RP1-251c21) covering FGFR4 is isolated, and it is confirmed that it covers the 5q35 breakpoint by FISH analysis. Thereafter, a BAC/PAC/cosmid-based physical map covering the breakpoint is constructed to validate additional genes around the breakpoint (FIG. 1a). The FISH analysis shows that RP1-118m12 and its cosmid subclones (c2b,c4D,c6A, and c6B) span the breakpoint (FIG. 1b). Another gene, JAZ (Genbank Accession No. XM 012279) is identified through draft/complete sequences (AC027314 for CTC-286c20 and AC008570 for CTC-549a4) within the physical map. The coding regions of JAZ are sequenced in the 12 patients, but no nucleotide change is found, either. BlastN searches using a partial genomic sequence (AC02314) corresponding to c6B identified sequences homologous to the mouse Nsd1 gene. Since Nsd1 encoding a nuclear receptor (NR) binding protein is possibly related to transcriptional regulation, its human ortholog, NSD1 becomes an attractive candidate gene, and is isolated. The isolated NSD1 has an 8,088-bp open reading frame and consists of at least 23 exons (Genbank accession No. AF395588).

The breakpoint is located within NSD1, because the FISH analysis using c6B gives split signals on both der(5) and der(8) chromosomes of the patient and each signal intensity is almost even (FIGS. 1a and b). FIG. 1a shows a physical map, wherein a heavy black line indicates BAC/PAC cosmid clones and red and blue lines indicate a clone covering the 5q35 breakpoint by FISH analysis, and complete genome sequences, respectively. Arrows indicate candidate genes. FIG. 1b shows a FISH analysis using a cosmid, c6B on chromosomes of the patient BP, wherein red and yellow arrows indicate signals on normal chromosome 5, and derivative chromosomes 5 and 8, respectively. Forty sets of primers are designed to amplify the entire coding region of the gene. A genomic DNA from a total of 38 unrelated normal patients with SS is analyzed by direct sequencing.

Figure 2:
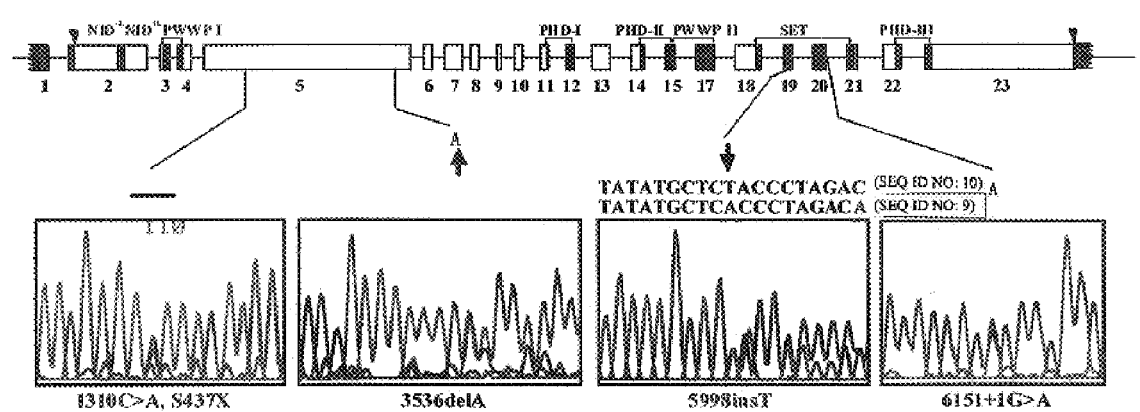
FIG. 2 is a view showing various mutations of NSD1.
Figure 3:
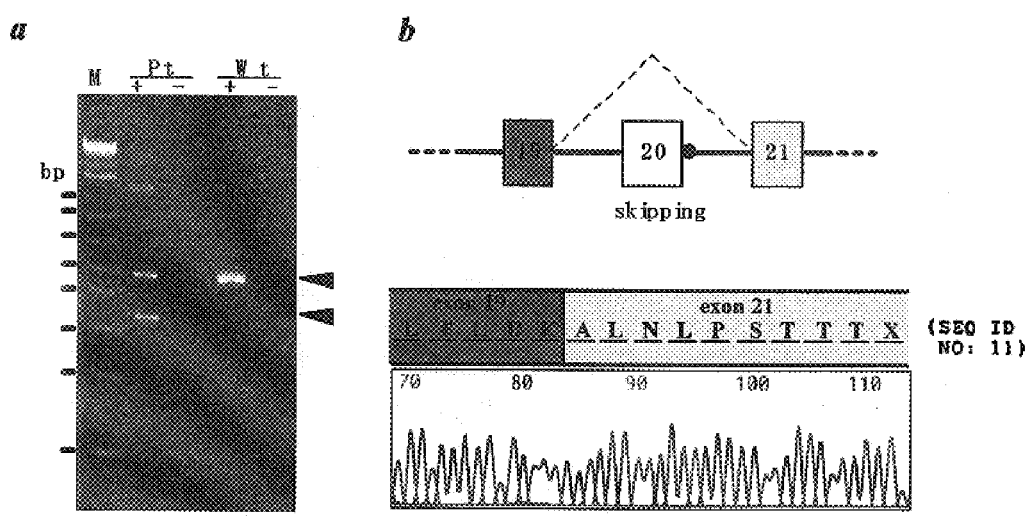
FIG. 3 is a view showing results on a direct sequence determination in an immortalizing lymphoblast cell line of a patient.
Figure 4:
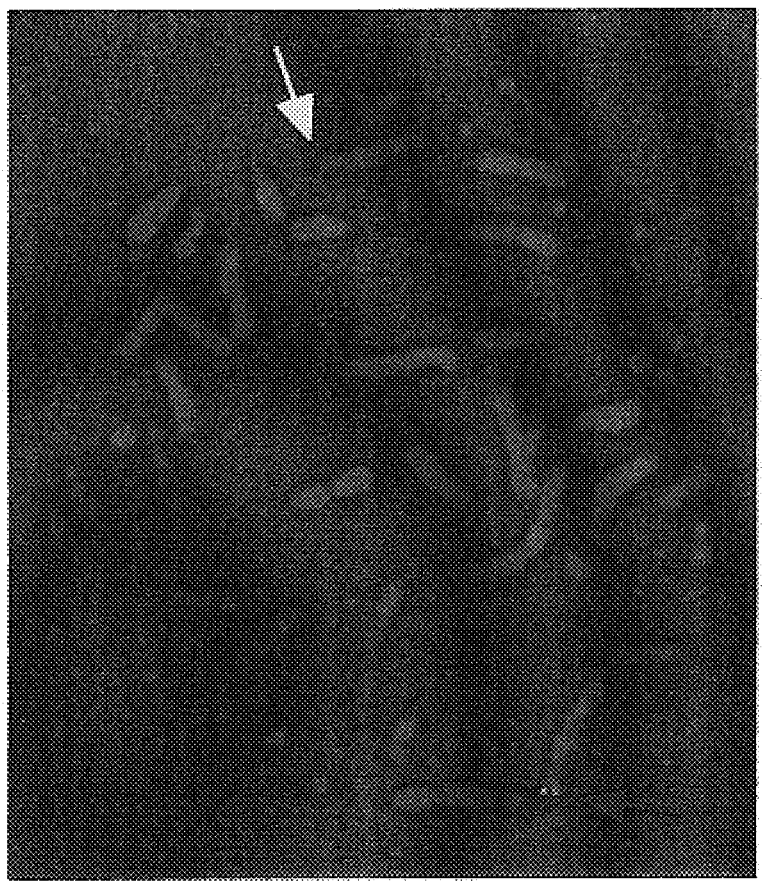
FIG. 4 is a view showing a result of FISH analysis.

Then, four different point mutations of NSD1 in four of 39 patients including patient BP is identified (FIG. 2, Table 1). FIG. 2 shows a genomic structure of NSD1 and mutations detected in the patients with Sotos syndrome. A particular region is shown as a colored box, wherein light blue is an NR-interaction domain ($NID^{-L}$), pink is an NR-interaction domain ($NID^{+L}$), blue is PHD finger domains, green is PWWP domains, and red is a SET domain. The mutations include a nonsense mutation (1310C->A, S437X) in exon 5, a one-base deletion (3536delA) in exon 5, a one-base insertion (5998insT) in exon 19, and a base substitution (6151+1G->A) at the splice donor site in intron 20. As their respective parents confirmed for paternity have no such changes, the four mutations are all de novo types. The TCA(Ser)->TAA(stop) nonsense mutation is predicted to lead a truncation of NSD1 protein(S437X) at amino acid position 437. The deletion (3536delA) leads to a premature stop codon at nt 3651–3653, and the insertion (5998insT) also results in a premature stop codon at nt 6022–6024. The splice site mutation (6151+1G->A) is predicted to skip exon 20, producing a smaller cDNA and resulting in a truncated protein added with only 9 amino acids after exon 19. The shorter cDNA deleting exon 20 is confirmed by RT-PCR and direct sequencing in the patient's immortalized lymphoblastoid cell line (FIG. 3). FIG. 3a shows results of RT-PCR analysis, wherein black and red arrows indicate a normal 471-bp product and an abnormal 329-bp product, respectively. Also, symbol Pt is a patient 24, symbol Wt is a normal control, symbol + is the use of a reverse transcriptase, and symbol − is no use of a reverse transcriptase. In FIG. 3b, an upper line shows exons 19, 20 and 21, and a small red circle indicates a mutation at a splice-donor site. A sequence analysis of the 329 bp product shows a skipping of exon 20, resulting in a frame-shift and a new stop codon at 10th codon of exon 21. Although five other base-substitutions (three synonymous and two non-synonymous changes) are identified in either exon 5 or exon 23, they are commonly observed in normal controls and are likely to be polymorphic, i.e. single nucleotide polymorphisms (SNPs)(Table 1). Surprisingly, 29 of the 39 patients show a homozygous pattern at all these five SNP locations. These data strongly suggest the presence of deletion involving NSD1, while the data in 12 normal control individuals are consistent with the Hardy-Weinberg equilibrium. The FISH analysis using RP1-118m12 as a probe detects a deletion in 20 (66.7%) of 30 patients whose metaphase and/or interphase cells are available (FIG. 4), wherein red and yellow arrows indicate a signal on normal chromosome 5 and no signal on the deleted chromosome 5, respectively. The FISH analysis suggests together with the data(4/38) for point mutations that 77% of SS patients in this series have NSD1 mutations (Table 1). All the changes identified are deletions (hemizygous) or heterozygous mutations causing protein truncation. Thus, it is most likely that haploinsufficency of NSD1 is the major cause of Sotos syndrome.

NSD1 is a bifunctional nuclear protein, acting as a nuclear receptor corepressor and as a coactivator by interacting with the ligand-binding domain of NRs. Human NSD1 has two distinct NR-interaction domains called $NID^{-L}$ and $NID^{+L}$, and other conserved domains such as SET (su(var)3-9, enhancer-of-zestem trutgirax), PWWP (proline-tryptophan-proline), and PHD (plant homeodomain protein) finger domains. The two protein truncation (PT) mutations (S437X and 3536delA) observed in SS patients may result in loss of PHD-I, PHD-II, PWWP-II, SET, and PHD-II domains. The one-bp insertion (5998insT) and the splice-site mutation (6151+1G>A) may lose SET and PHD-III domains (FIG. 2). These findings suggest that the minimal deletion of the SET and PHD-III domains involved in the protein truncations in SS patients are functionally critical in this protein.

The PHD finger domain may interact with other proteins and be involved in chromatin regulation.

Recently, an NSD1-derived chimeric protein is isolated from a childhood acute myeloid leukemia (AML) associated with t(5;11)(q35;p15.5) in which NSD1 is fused with NUP98 at NSD1 intron 5. In the patient BP, the chromosome break is presumed to be located at intron 2. Therefore, this may suggest that mutation types are different between the two conditions, i.e. constitutional protein truncation mutation versus somatic mutation with fusion-gene formation.

NSD1 shows 75% homology at nucleotide level to WHSC1 (NSD2) isolated from a minimum deletion region of the 165-kc Wolf-Hirschhorn syndrome (WHS). The WHS (OMIM 194190) is characterized by multiple anomalies, severe growth retardation, mental defect, and hemizygous deletion (haploinsufficiency) of 4 p. Further, NSD2 cause a type of multiple myeloma when being fused with the IgH gene by t(4;14). It is likely that both genes (NSD1 and NSD2) are important for human growth and brain development as well as for cell growth.

Since SS is thought to be genetically heterogeneous, as SS is described in a mother and two daughters, two brothers, and three sibs (monozygotic twin girls and their brother), autosomal recessive inheritance is postulated. Also, the other patients with de novo t(3;6)(p21;p21), mos dup (20) (p11.2–p12.1)[12/66] and t(2;12)(q33.3;q15) mat are described. Thus, either chromosomal breakpoints or segments are suggested to harbor another SS locus.

However, the aforementioned data indicate that the majority (up to 77%) of SS patients have an NSD1 mutation. This finding of NSD1 defects in Sotos syndrome will facilitate the diagnosis of SS and shed light in understanding the mechanisms of mental retardation and growth disorders in the human.

Physical Map Construction

The RPCI-1, -3, human PAC libraries are screened by PCR using STSs as described previously. Cosmid subclones are prepared from a PAC spanning the breakpoint. A purified PAC DNA is isolated by using Midi-Prep™ columns (Qiagen, Chatsworth, Calif.) and partially digested with Sau3AI. The SuperCos1 cosmid vector is prepared according to the manufacture's instructions (Stratagene, La Jolla, Calif.) and ligated to the digested PAC DNA by using T4DNA ligase. This ligation reaction products are packaged by using the Gigapack III gold extract (Stratagene) and transfected into XL1-Blue MR host cells (Stratagene). Contigs are constructed by means of STS content mapping using PCR with reference to draft/complete genomic sequences. BAC/PAC/cosmmid DNA is extracted with Midi-Prep™ columns. New STSs are generated from clone-end sequences using T7/SP6 primers for BAC or T7/T3 for cosmid. Sequencing reactions are carried out with ABI Prism™ BigDye Terminator Cycle Sequencing Ready Reaction Kit (PE Applied Biosystems, Foster, Calif.) using 2 μg of BAC/PAC DNA or 1 μg of cosmid DNA as a template and 40 pmol primer.

Cycle sequencing is performed for 50 cycles at 96° C. for 10 seconds, 50° C. for 5 seconds, and 60° C. for 4 minutes.

FISH Analysis

The FISH analysis using BAC/PAC/cosmid DNA is performed on metaphase chromosomes and/or interphase cells from SS patients and a normal control. A cloned DNA is labeled with SpectrumGreen™-11-dUTP or SpectrumOrange™-11-dUTP (Vysis, Downers Grove, Ill.) by a nick translation, and denatured at 76° C. for 10 minutes. Probe-hybridization mixtures (10 μl) are applied on the chromosomes, incubated at 37° C. for 16 hours, and then washed as described previously. A fluorescence photomicroscopy is performed under a Zeiss Axioskop microscope equipped with a quad filter set with single band excitation filters (84000, Chroma Technology Corp., Brattleboro, Vt.). Images are collected and merged by using a cooled CCD camera (TEA/CCD-1317-G1, Princeton Instruments, Trenton, N.J.) and IPLab/MAC software (Scanalytics, Inc., Fairfax, Va.).

Patient and Parent Samples

DNA is extracted from peripheral blood leukocytes or lymphoblastoid cell lines of sporadic patients with Sotos syndrome after an informed consent is obtained. In several cases, the samples are also collected from their parents. All but one patient (a Japanese-Pakistani) is of Japanese origin. Experimental protocols are approved by the Ethical Committee for Gene Research of Nagasaki University School of Medicine.

Mutation Analysis

Twenty-two NSD1 exons (exons 2–23) covering the coding region are amplified by PCR. The PCR is cycled 35 times at 95° C. for 30 seconds, 50° C. for 30 seconds, 72° C. for 1 minute in a volume of 50 μl, containing 1×PCR buffer with 1.5 mM MgCl$_2$, 0.2 mM each dNTP, 1 μM each primer and 2.5U TaqGold polymerase (PE Applied Biosystems).

PCR products are purified by using the QIAquick PCR purification kit (Qiagen, Chatsworth, Calif.) and sequenced on both strands with BigDye Terminator chemistry by a standard protocol (PE Applied Biosystems) as described preciously.

RT-PCR Analysis

A total RNA is prepared from lymphoclastoid cell lines established from a patient and a normal control using the Trizol reagent (Gibco-BRL, Gaithersburg, Md.).

A reverse transcription is carried out by using random hexamers and Superscript™ first-strand synthesis system for RT-PCR (Gibco-BRL) according to the manufacturer's protocol. The cDNAs are amplified by PCR with primers, NSD1PT1F, 5'-ATTTGTGAATGAGTATGTGG-3' (SEQ ID NO: 7) (nt 5898–5917) and NSD1RT1R, 5'-CTAAAA-CACTCATCTTCTCG-3' (SEQ ID NO: 8) (nt 6349–6368) for 35 cycles at annealing temperature of 48° C. The PCR product is directly sequenced.

Genbank Accession Numbers

Human NSD1, AF395588; NSD2, XM 055926; FGFR4, XM 030308; JAZ, XM 012279; mouse Nsd1, NM 008739; BAC clone CTC-286c20, AC027314, CTC-549a4, AC008570.

TABLE 1

NSD1 mutations identified in patients with Sotos syndrome and SNPs of NSDI

| Patient or SNP | Exon or intron | Type of mutation | Inheritance | Consequence |
| --- | --- | --- | --- | --- |
| Patient BP | intron 2* | translocation | de novo | gene disruption |
| Patients 1–20 | | deletion | de novo | missing gene |
| Patient 21 | exon 5 | 1310C –> A | de novo | S437X |
| Patient 22 | exon 5 | 3536delA | de novo | Protein truncation |
| Patient 23 | exon 19 | 5989insT | de novo | Protein truncation |
| Patient 24 | Intron 20 | 6165 + 1G –> A | de novo | Protein truncation |
| SNP 1 | exon 5 | 1482C –> T | | Synonymous |
| SNP 2 | exon 5 | 1749G –> A | | Synonymous |
| SNP 3 | exon 5 | 1840G –> T | | V614L |
| SNP 4 | exon 5 | 2176T –> C | | S727P |
| SNP 5 | exon 23 | 6829C –> T | | Synonymous |

SNP, single nucleotide polymorphism;
*estimated by FISH data

EXAMPLE 2

Next, an object is examined by using the probe comprising sequence number 5 and 6 of the sequence table as to whether or not they are a patient suffered from Sotos syndrome. The FISH analysis is carried out by the same manner as the example 1.

Specifically, FISH analysis is carried out by using RPCI-11 147K7 and RPCI-11 1006E8. RPCI-11 147K7 and RPCI-11 1006E8 can be easily available from genome databases.

As a result of this, a deletion is confirmed at 60% of a patient suffered from Sotos syndrome. Therefore, it is found that a gene diagnosis can be carried out by using the present probe.

Conclusively, a confirmed diagnosis whether or not a patient is suffered from Sotos syndrome may be carried out by the FISH analysis in a similar manner wherein a nucleic acid concerning NSD1 region of the present invention is used as a probe.

The nucleic acid according to the invention and the probe using such a nucleic acid have an advantageous effect that they can be used as a gene diagnosis and a gene therapy.

Particularly, according to the invention using a fluorescence in situ hybridization, the RI equipment is useless, and the operating procedure is simple, and it is excellent in a point that in-depth mapping is exactly carried out on a chromosome band for a short time (2 days), so that it is also useful for a rapid and safety gene diagnosis.

What is claimed is:

1. A screening method for diagnosing Sotos Syndrome comprising contacting a probe with a sample which is being evaluated for indication of Sotos Syndrome, said probe being derived from a genomic DNA sequence including an exon 1, an exon 2 and an intron of NSD1;
   (a) a nucleic acid comprising a base sequence shown in base numbers 1–39726 of SEQ ID NO: 1, or
   (b) a modified nucleic acid wherein a part of the bases 1–39726 of SEQ ID NO: 1 has been deleted or substituted, or to which at least one base has been added, said modified nucleic acid having a homology of 80% for said base sequence shown in base numbers 1–39726 of SEQ ID NO: 1.

2. The method according to claim 1, wherein the screening is carried out by using at least one selected from the group consisting of in situ hybridization method, Southern blotting method, and a base sequence determination method.

3. The method according to claim 2, wherein the in situ hybridization method is a fluorescence in situ hybridization method.

* * * * *